United States Patent [19]

Quay et al.

[11] Patent Number: 5,039,511
[45] Date of Patent: Aug. 13, 1991

[54] AMYLOIDOSIS AND ALZHEIMER'S DISEASE DIAGNOSTIC ASSAY AND REAGENTS THEREFOR

[75] Inventors: Steven C. Quay, Los Altos Hills; Scott M. Rocklage, Saratoga; Warren K. Miller, Cupertino, all of Calif.

[73] Assignee: Salutar, Inc., Sunnyvale, Calif.

[21] Appl. No.: 582,152

[22] Filed: Sep. 14, 1990

Related U.S. Application Data

[60] Division of Ser. No. 510,461, Apr. 17, 1990, which is a division of Ser. No. 178,402, Apr. 6, 1988, Pat. No. 4,933,156, which is a continuation-in-part of Ser. No. 35,837, Apr. 8, 1987, abandoned.

[51] Int. Cl.$^5$ ............... A61K 49/02; C07D 277/62
[52] U.S. Cl. ............................... 424/1.1; 548/178
[58] Field of Search ............... 424/1.1; 548/178, 179, 548/180

[56] References Cited

U.S. PATENT DOCUMENTS 4,435,570 3/1984 Nishimura et al. ............ 424/1.1 X

Primary Examiner—John S. Maples
Attorney, Agent, or Firm—Cushman, Darby & Cushman

[57] ABSTRACT

The presence and location of amyloid deposits in an organ or body area of a patient is effected by intravenous administration of novel radioactive iodine-labeled amyloid binding compounds and preferably $^{123}$I-labeled compounds to the patient and sensing radiation emitted from the organ or body area. Novel non-radioactive iodine substituted amyloid binding compounds and amyloid binding compounds which are readily iodinated are further aspects of the invention

4 Claims, No Drawings

AMYLOIDOSIS AND ALZHEIMER'S DISEASE DIAGNOSTIC ASSAY AND REAGENTS THEREFOR

RELATIONSHIP TO COPENDING APPLICATION

This application is a division of copending application Ser. No. 510,461, filed Apr. 17, 1990, which in turn is a division of copending application Ser. No. 178,402, filed Apr. 6, 1988 now U.S. Pat. No. 4,933,156, which in turn was a continuation-in-part of copending application Ser. No. 035,837, filed Apr. 8, 1987, now abandoned.

FIELD OF THE INVENTION

This invention relates to novel compounds and their use for diagnosing Alzheimer's disease and other diseases characterized by presence of amyloidosis. In particular, this invention relates to compounds which selectively bind to amyloid structures in the body and which can be readily iodinated, the radioactive iodine substituted derivatives thereof, and the diagnosis of amyloid associated diseases with the radiolabeled derivatives.

BACKGROUND OF THE INVENTION

Alzheimer's disease (AD) is the most frequent cause of dementia in the United States and is currently the fourth most common cause of death. The disease can strike persons as young as 40-50 years of age and affects over three million individuals. The origin of the disease is unknown, and because the presence of the disease is difficult to determine without invasive biopsy, its time of onset is unknown. The condition is characterized by impairments in memory, cognition, language and mobility, and these conditions become progressively more severe with time. Neuropathological examination of the brains of affected individuals discloses the presence of several characteristic abnormalities: neuritic plaques consisting of abnormal neuronal axon terminals associated with a core of extra-cellular amyloid protein; neurofibrillary tangles comprised of bundles of cross-linked protein filaments which have accumulated in the neuronal cell bodies; and granulovacuolar degeneration which consists of intercellular vacuoles present mostly in hippocampal pyramidal neurons.

In addition, a strong correlation has been found between the density of amyloid-containing plaques in the cortex of AD victims at autopsy and the severity of their cognitive defects. Until recently, diagnosis of AD was based on clinical criteria involving clinical diagnosis of physical and mental impairment and determination that other diseases with the same characteristics were not the cause of the impairments.

Post-mortem slices of brain tissue of victims of Alzheimer's disease have been shown to exhibit the presence of amyloid (an amorphous mixture of protein, carbohydrate and lipid complexes) in the form of proteinaceous extracellular cores of the neuritic plaques characteristic of the disease. The amyloid cores of such senile plaques are composed of microscopic fibrils whose protein is arranged in a predominately $\beta$-pleated sheet configuration. AD plaque amyloid appears to contain one or more characteristic protein constituents, and some have been isolated and purified. Vascular deposits of amyloid fibrils in non-Alzheimer's amyloidoses have been shown to be derived from an abnormal serum protein by Glenner, G. *New Eng. J. Med.* 302:1283-1291 (1980). The genetic locus for the amyloid protein has been localized to chromosome 21 as reported by George-Hyslop et al, *Science.* 235:885-890 (1987) and Tanzi et al, *Science.* 235:880-884 (1987). Isolation and partial sequencing of the gene has been reported by Goldaber et al, *Science.* 235:877-880 (1987), and partial sequencing of at least one of the amyloid AD proteins has been reported by Glenner, G. et al, *Biochemical and Biophysical Communications.* 120:885-890 (1984).

More recently, immunoassay methods have been developed for detecting the presence of neurochemical markers in AD patients and to detect an AD related amyloid protein in cerebral spinal fluid as summarized by Warner, M. *Anal. Chem.* 59:1203A-1204A (1987). These new methods, while being a major advance over the earlier method for diagnosing AD, have not proven to detect AD in all patients, particularly at early stages of the disease.

Because Alzheimer's disease is slow in onset, can first appear as early as the fifth decade of life, and is progressive in nature, the efficiency of a cure could critically depend upon early detection. Additionally, the value of any new therapy in alleviating or curing the disease could be better ascertained if a rapid, safe and effective diagnostic procedure were available to monitor the progress of AD patients following treatment.

The most advanced diagnostic tests for AD detection developed to date determine the AD-associated amyloid protein in spinal fluid using an antibody binding selectively therewith. A spinal tap procedure is required to obtain a sample for testing. Such a procedure is painful, invasive, potentially dangerous, costly, and the patient often must be hospitalized overnight for observation.

Cerebrovascular amyloidosis has been observed only in patients with Alzheimer's disease and adult Down's syndrome by Glenner, G., COLD SPRING HARBOR SYMPOSIUM. pp. 137-144 (1983) and a familial Icelandic cerebrovascular amyloidosis syndrome by Cohen, et al, *J. Exp. Med.* 158:623-628 (1983). The latter conditions have characteristics other than dementia which are easily determined and can be distinguished from AD. Amyloid thus can be used as a chemical marker for the disease.

Non-cerebral amyloid is an extracellular, amorphous, eosinophilic material most commonly arising as a consequence of chronic inflammatory disease of long standing. Spleen, liver, kidneys, adrenals, lymph nodes and pancreas are the organs usually affected. Gratuitously, amyloid of this type was referred to as secondary or typical. Primary, or atypical amyloid is usually found in muscle and the cardiovascular system, but may be more conveniently diagnosed in rectal, skin or gingival biopsies. It arises in the absence of any obvious predisposing inflammatory disease.

DESCRIPTION OF THE PRIOR ART

Congo Red and other benzidine-type dyes such as Congo Corinth, Benzopurpurin 4B, Vital Red, and Trypan Blue stain amyloid selectively as reported by Puchtler, H. et al, "On the binding of Congo Red by amyloid." *J. Histochem. Cytochem.* 10:35-364 (1962). The stained amyloid is characterized by a dichroic appearance, the Congo Red stained amyloid showing a green polarization color. Puchtler, H. et al, "Application of thiazole dyes to amyloid under conditions of direct cotton dyeing: correlation of histochemical and chemical data." *Histochem.* 77:431–445 (1983) describes amyloid staining and fluorescence characteristics of Phorwhite BBU, Thioflavine S, Congo Red, Diphenyl Brilliant Yellow 8G, Clayton Yellow, Thiazol Yellow, Thioflavine T, Seto Flavine T, Erie Pink 2B, Thiazine Red R, Geranine G, Diphenyl Chlorine Yellow FF, Direct Yellow 29, Sirius Supra Yellow 5G and Solophenyl Yellow FFL. Studies of thiazole dyes, Primulin, Thioflavine S and Thioflavine T as amyloid staining dyes were reported by Kelenyi, G., "On the histochemistry of azo group-free thiazole dyes." *J. Histochem. Cytochem.* 15:172–180 (1967).

The dichroic binding was determined to be the result of the β-pleated sheet structure which is the common characteristic of amyloid proteins, independently of the diverse chemical structure of the various amyloid tissues by Glenner, G. "Amyloid deposits and amyloidosis: The β-fibrilloses (first of two parts)." *New England. J. Med.* 302:1283–1292 (1980).

The non-invasive technique for diagnosis of amyloidosis comprising the Congo Red uptake method of Bennhold was described as inconstant and of dubious diagnostic value by Glenner, G., "Amyloid deposits and amyloidosis: the β-fibrilloses (second of two parts)." *New England J. Med.* 302:1333–1343 (1980). He also describes and lists the diseases associated with amyloidosis and their diverse origin. The common factor for the diseases was the β-pleated structure of the amyloid proteins, and the causes for these deposits appeared to be diverse.

Efforts to improve the method of Bennhold first studies the effects of different dosing schedules and selecting different times for determining depletion of the Congo Red levels in serum by Unger, P. et al, "Study of the disappearance of Congo Red from the blood of non-amyloid subjects and patients with amyloidosis." *J. Clin. Invest.* 27:111 (1948). In efforts to reduce the amount of Congo Red required in this procedure, Knorpp, C. et al, "Radiosulfur ($S^{35}$) labeled Congo Red dye." *J. Nucl. Med.* 1:23–30 (1960) synthesized a radiosulfur-labeled Congo Red dye and investigated it use in diagnosing amyloidosis. $^{35}S$ (half life 87.2 days) was selected as the only inorganic tracer suitable for the intended synthesis. The plasma level was then quantified by measuring the radioactive label.

Tubis, M. et al, "The preparation and use of radioiodinated Congo Red in detecting amyloidosis." *J. Amer. Pharm. Ass.* 49:422 (1960) describes synthesis of a Congo Red substituted at one or more of the 3,3',5 and 5' positions. In one procedure, the Congo Red was prepared by diazotizing the radioiodinated benzidines and coupling with sodium naphthalate. In another procedure of direct radioiodination, the Congo Red was refluxed in a chloroform solution containing 0.0163 mg of $^{131}ICl$ for 8 to 12 hours followed by dialysis or column treatment with an anion exchange resin in either the OH or Cl form. These methods are not suitable for preparing a radiolabeling with $^{123}I$ which has a half-life of 13.1 hours. $^{123}I$ has an optimum emission spectrum of 0.1590 MeV representing 83%. Other radioactive forms of iodine such as $^{131}I$ have longer half-lives, increasing the patient exposure to radiation and/or more than one significant emission energy spike, severely limiting the value for diagnostic imaging. Tubis, M. et al, "The use of radioiodinated Congo Red in the study of amyloidosis." *Nuklear Medizin.* 3:25–38 (1962) studied the use of $^{131}I$-labeled Congo Red in the diagnosis of amyloidosis in humans. The use of the radiolabeled Congo Red permitted easy quantification of the disappearance of the dye. However, $^{131}I$ has multiple decay energy emissions and an undesirably long half-life of 8.1 days, and it is not suitable for routine in vivo diagnostic use. The radioactive label was used in serum depletion and photoscans of amyloid affected organs.

Kaye, M. et al, "A radioiodinated azo dye with affinity for amyloid: a preliminary report." *Canad. Med. Ass. J.* 30:694 (1964) reported developing a Trypan Blue substituted at the 8-position with a radioactive iodine compound using a "Sandmeyer reaction". Use of the product in selectively staining amyloid tissue and metabolic studies were reported.

OBJECTS AND SUMMARY OF THE INVENTION

One object of this invention is the provision of compounds which selectively bind with amyloid in vivo and which can be readily labeled with radioactive iodine.

It is another object of this invention to provide radioactive iodine labeled amyloid binding compounds which can be administered for the diagnosis of Alzheimer's disease and other amyloidosis.

It is still a further object of this invention to provide a non-invasive diagnostic method for diagnosing diseases characterized by amyloidosis using radiolabeled compounds which selectively bind with amyloid tissues.

The radioiodinated compounds of this invention are selected from the group of compounds represented by Formulas I, II, III and IV and their water-soluble, pharmaceutically acceptable salts wherein I* represents a radioactive iodine isotope. The compounds of Formula I are represented by the following formula:

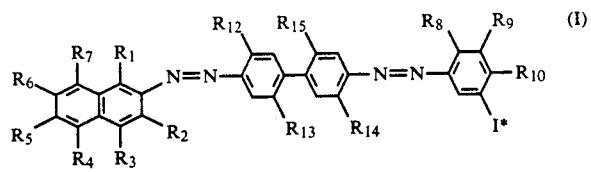

wherein
$R_1$ is amino or hydroxy;
$R_2$, $R_3$, $R_4$, $R_5$ and $R_6$ are hydrogen or sulfo, with the proviso that not more than two of $R_2$, $R_3$, $R_4$, $R_5$ and $R_6$ are sulfo and sulfo is not present on adjacent carbons;
$R_7$ is hydrogen or hydroxy;
$R_8$, $R_9$ and $R_{10}$ are hydrogen, hydroxy, carboxy or lower alkyl esters thereof, methyl, or methoxy;
$R_{12}$ and $R_{14}$ are each independently hydrogen, methyl, chloro, methoxy, carboxy or a lower alkyl ester thereof, or nitro; and
$R_{13}$ and $R_{15}$ are each independently hydrogen or sulfo.

The compounds of Formula II are represented by the following formula:

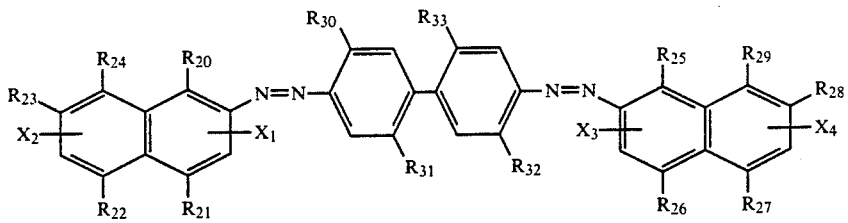

wherein
- $R_{20}$, $R_{24}$, $R_{25}$ and $R_{29}$ each independently are hydrogen, hydroxy or amino, with the proviso that $R_{24}$ is not the same as $R_{20}$ and $R_{29}$ is not the same as $R_{25}$;
- $R_{21}$, $R_{22}$, $R_{23}$, $R_{26}$, $R_{27}$ and $R_{28}$ each independently are hydrogen or sulfo, with the proviso that not more than two of $R_{21}$, $R_{22}$ and $R_{23}$ is sulfo and not more than two of $R_{26}$, $R_{27}$ and $R_{28}$ is sulfo, and sulfo is not present on adjacent carbons;
- $R_{30}$ and $R_{32}$ are each independently hydrogen, methyl, chloro, methoxy, carboxy or a lower alkyl ester thereof, or nitro;
- $R_{31}$ and $R_{33}$ are each independently hydrogen or sulfo;
- $X_1$, $X_2$, $X_3$ and $X_4$ are each independently hydrogen or I*, with the proviso that $X_1$ is hydrogen when $R_{21}$ is sulfo, $X_2$ is hydrogen when $R_{22}$ and $R_{23}$ is sulfo, $X_3$ is hydrogen when $R_{26}$ is sulfo, and $X_4$ is hydrogen when $R_{27}$ or $R_{28}$ is sulfo.

The compounds of Formula III are represented by the following formula:

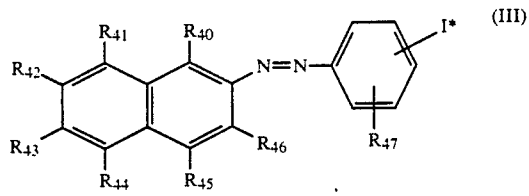

wherein
- $R_{40}$ and $R_{41}$ are hydroxy or amino, and $R_{40}$ and $R_{41}$ are not the same group;
- $R_{42}$, $R_{43}$, $R_{44}$, $R_{45}$, and $R_{46}$ are hydrogen or sulfo; one or two of $R_{42}$, $R_{43}$, $R_{44}$, $R_{45}$, and $R_{46}$ are sulfo; and sulfo is not present on adjacent carbons; and
- $R_{47}$ is hydrogen, methyl or carboxy.

The compounds of Formula IV are represented by the following formula:

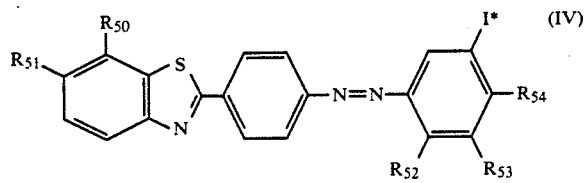

wherein
- $R_{50}$ is hydrogen or sulfo;
- $R_{51}$ is methyl or carboxy; and
- $R_{52}$, $R_{53}$ and $R_{54}$ each are hydrogen, hydroxy, carboxy or lower alkyl esters thereof, methyl, or methoxy.

In compounds of this invention, the preferred radioactive form of iodine is $^{123}I$.

The non-radioactive iodine and uniodinated precursors of the Compounds of Formulas I, II, III and IV wherein I* is replaced by hydrogen or non-radioactive I are also intermediate compounds of this invention.

The method of this invention for determining the presence and location of amyloid deposits in an organ or area of a patient comprises intravenous administration of an imaging effective quantity of a compound of Formulas I, II, III or IV, or a pharmaceutically acceptable, water-soluble salt thereof to the patient; and sensing radiation emitted from the organ or area being examined.

DETAILED DESCRIPTION OF THE INVENTION

The method of this invention for determining the presence and location of amyloid deposits in an organ or area of a patient comprises intravenous administration of an imaging effective quantity of a compound of Formulas I, II, III or IV ("Imaging Compounds"), or a pharmaceutically acceptable, water-soluble salt thereof to the patient; and sensing radiation emitted from the organ or area being examined.

The imaging compounds are formed from precursor compounds which can be readily and quickly iodinated with I*.

The bisdiazobenzidine compounds precursors of Formula VII are formed from the respective, known diamino compounds of Formula VI by the following reaction sequence.

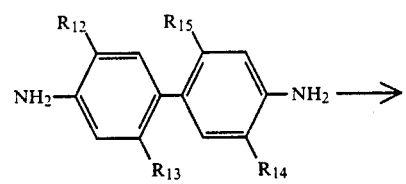

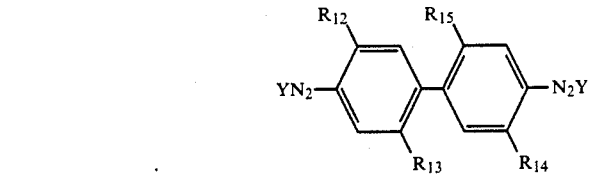

wherein $R_{12}$, $R_{13}$, $R_{14}$ and $R_{15}$ are as previously described with respect to Formula I and Y is $Cl^-$ or $BF_4^-$. The diamino compounds of Formula VI are known in the art. These are diazotized by reaction with two molar equivalents of sodium nitrite in aqueous acid solution (HCl, H$_2$SO$_4$, or the like) to yield the diazo compounds of Formula VII, a starting material for several groups of diazo compounds of this invention.

In general, all of the aniline and benzidine compounds described herein can be diazotized in aqueous acid (e.g., HCl, H$_2$SO$_4$, etc.) with sodium nitrite (NaNO$_2$). One equivalent of acid per amine group is used to generate the acid salt. The mixture is maintained at $-5°$ C. to 15° C. in an ice/solvent bath. One additional equivalent of acid per amine group is added to generate nitrous acid from added sodium nitrite. The aqueous diazonium salt is used within 10 to 20 minutes of preparation.

An alternate method of diazotization which can be used for neutral aromatic amines comprises the reaction of the amine with 1.5 to 2 molar equivalents of boron trifluoride etherate in THF at $-5°$ C. to 15° C., followed by the addition of one molar equivalent of t-butyl nitrite per amine group. The resulting tetrafluoroborate salt precipitates from the solution and can be isolated and stored at temperatures below 0° C. The salts can be dissolved in a polar organic solvent such as alcohol and added to the selected substrate for diazo coupling.

The compounds of Formula I are formed in two stages. The diazo compounds of Formula VII are reacted with one molar equivalent of the sulfonic acid compounds of Formula VIII in aqueous solution.

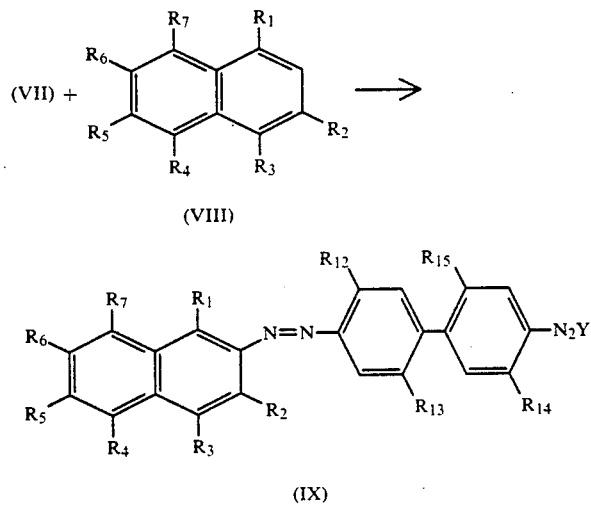

In the Formulas VIII and IX, $R_1$, $R_2$, $R_3$, $R_4$, $R_5$, $R_6$, $R_7$, $R_{12}$, $R_{13}$, $R_{14}$ and $R_{15}$ are as identified above with respect to Formula I and Y is an anion such as Cl$^-$ or BF$_4^-$. the reaction product is then reacted with a molar equivalent of an iodophenyl compound of Formula X, yielding the compounds of Formula XI.

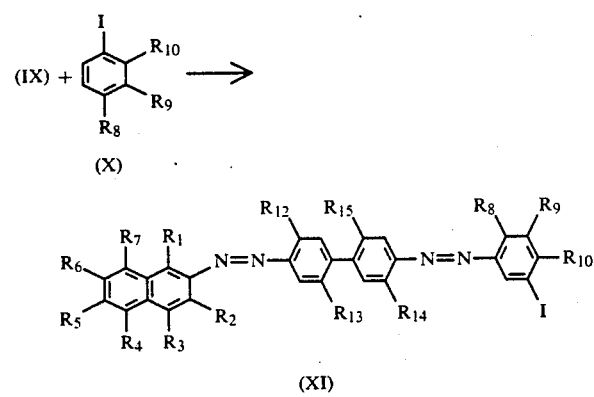

In Formulas X and XI, $R_1$, $R_2$, $R_3$, $R_4$, $R_5$, $R_6$, $R_7$, $R_8$, $R_9$, $R_{10}$, $R_{12}$, $R_{13}$, $R_{14}$ and $R_{15}$ are as identified above with respect to Formula I.

The diazo coupling reactions used to form the compounds of this invention involve the coupling of diazo compounds to aromatic amines and phenols. In general, the coupling reactions are carried out at $-5°$ C. to 20° C. in aqueous or aqueous alcohol solutions over a reaction period of from 10 minutes to 2 hours. The positions of coupling are determined by both steric factors and pH of the reaction solution. To achieve coupling ortho or para to an amine group, the solution is maintained in a pH range of about from 3 to 7. To achieve coupling ortho or para to a hydroxy group, the solution is maintained at pH from 8 to 11. When two diazo couplings are to be effected, for example with bisdiazobenzidines, the less reactive substrate is preferably coupled first. If acid and base couplings are required, the acid coupling is effected first to avoid the excessive decomposition of the diazonium group which can occur in basic solutions. When more than one activated ring position is available for coupling, the coupling usually occurs at the less sterically hindered position. Details of diazo coupling reactions are provided by Zollinger, H., AZO AND DIAZO CHEMISTRY: ALIPHATIC AND AROMATIC COMPOUNDS. New York: Interscience Publishers (1961), the entire contents of which are hereby incorporated by reference.

The radioiodinated compounds of Formula I are formed by iodide exchange of the compounds of Formula XI in absolute ethanol using NaI*, where I* represents a radioactive form of iodine.

$$(XI) + NaI^* \rightarrow (I)$$

In general, any of the azo dyes with an available activated aromatic ring position can be directly iodinated by electrophilic substitution. This is effected by reacting the dye with a suitable source of iodine such as iodine monochloride (ICl), or a 1:1 mixture of NaI and an oxidizing agent such as Chloramine-T, t-butyl hypochlorite, hydrogen peroxide, and the like, in a polar solvent such as an alcohol, DMF, water, etc. The iodination can occur either para or ortho to a hydroxy or amine group.

In general, the azo dyes can be radioiodinated either by direct iodination of non-iodinated azo dyes, as described above, using a source of radioactive iodine ($^{125}$I, $^{123}$I, etc.) and preferably $^{123}$I or by iodine exchange with non-radioactive iodine groups on dyes using sources of the radioactive iodine, as described above for radioiodinating the iodine substituted compounds of Formula XI. The exchange is carried out in a polar solvent such as alcohols, DMF, water, acetic acid, and the like at 100° C. to 200° C. in a sealed ampule for from 30 minutes to 24 hours. The concentration of dye in 1 to 2 mL of solvent is at least 0.1M (or saturated), with 0.2 to 10 mCi of carrier free radioactive iodide as NaI*.

The anionic acid dyes (sulfonates, carboxylates, etc.) can be purified by reverse phase thin layer chromatography (RPTLC) on C$_{18}$-silica gel plates such as (20×20 cm Whatman KC18F, 200 μm thick) eluting with a mixture of 80:20:0.2 v/v/v methanol:water:trifluoracetic acid. By repeating the above procedure on the same sample, radiochemical purities greater or equal to 99 percent can be obtained.

The non-ionic dyes can be purified by normal phase thin layer chromatography (NPTLC) ON 60A silica gel plates (Whatman Silica 60A (60 Angstroms), PK6F 20×20 cm, 250 μm thickness) eluted with dichloromethane/methanol mixtures of 50:50 to 90:10 v/v, or toluene/ethyl acetate mixtures of 80:20 v/v.

Purifications can also be carried out by HPLC or gravity column methods. A complete description of dye chromatography is given by Venkataraman, K., THE ANALYTICAL CHEMISTRY OF SYNTHETIC DYES. New York: John Wiley & Sons (1977), the entire contents of which are hereby incorporated by reference in their entirety.

The compounds of Formula II are synthesized by the following procedure.

The substituted naphthalene sulfonic acids of Formula XII are known compounds. The bis-diazobenzidine of Formula VII is added to the aqueous solution containing at least two molar equivalents of the naphthalene sulfonic acid of Formula XII at pH 4 to 6.5 to form the amyloid binding diazo compounds of Formula XIV.

Formula II. Alternatively, if a non-radioactive form of iodine is used and the iodine substituent of the compounds of Formula XIV are non-radioactive, the product can be readily labeled with radioactive iodine by iodide exchange in absolute ethanol using NaI* as described above.

$$(XIV) + NaI^* \rightarrow (II)$$

The products are purified by conventional procedures as described above.

The compounds of Formula III can be synthesized by reacting a compound of Formula VIII with the diazoiodobenzene of Formula XV according to the following procedure to form the iodinated diazo amyloid binding compounds of Formula XVI.

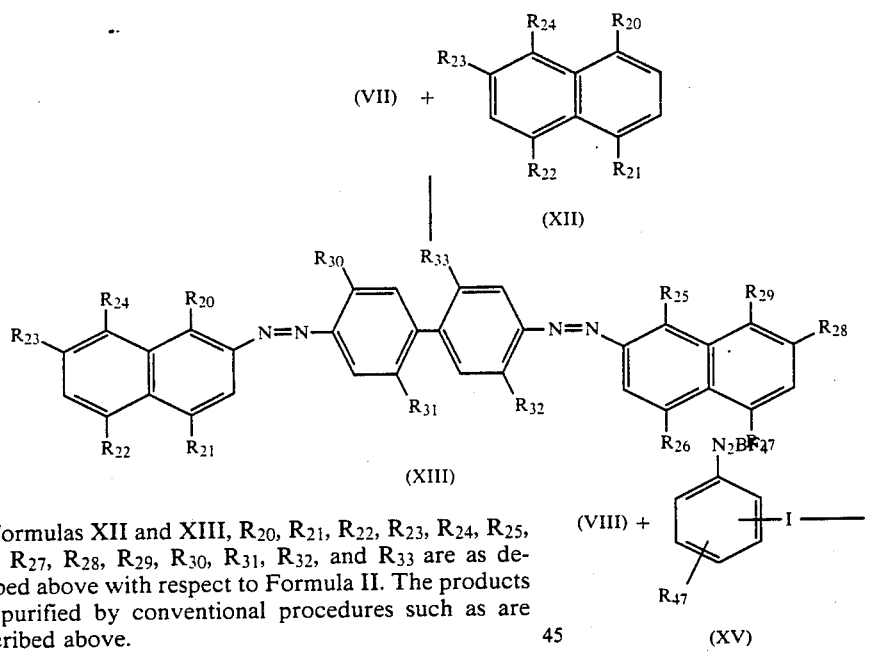

In Formulas XII and XIII, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, and $R_{33}$ are as described above with respect to Formula II. The products are purified by conventional procedures such as are described above.

The compounds of Formula XIII are readily iodinated by reaction with iodine monochloride or a 1:1 mixture of Chloramine-T and sodium iodide in aqueous methanol for one hour, the molar ratios of the iodine compound determining whether the reaction product of Formula XIV is to be mono-iodinated or di-iodinated.

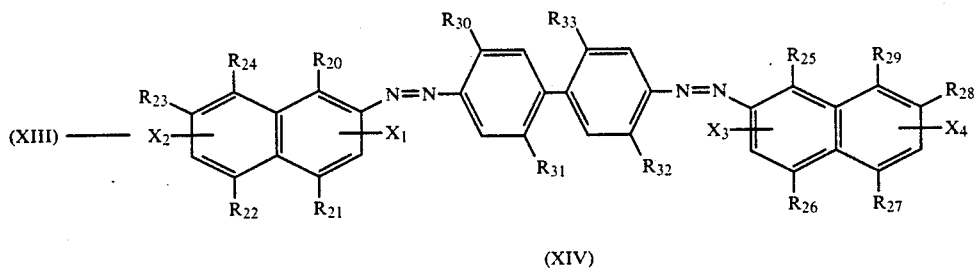

In Formula XIV, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $X_1$, $X_2$, $X_3$ and $X_4$ are as described above with respect to Formula II.

In the above procedure, the iodine source can be radioactive iodine to directly yield the compounds of

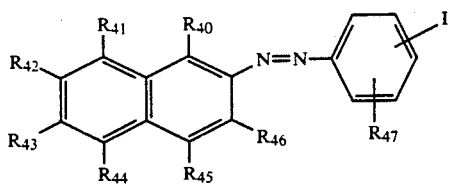

(XVI)

In Formulas XV and XVI, $R_{40}$, $R_{41}$, $R_{42}$, $R_{43}$, $R_{44}$, $R_{45}$, $R_{46}$ and $R_{47}$ are as described above with respect to Formula III.

The diazo coupling reaction is carried out as described above.

In the above procedure, the iodine source can be radioactive iodine to directly yield the compounds of Formula III. Alternatively, if a non-radioactive form of iodine is used and the iodine substituent of the compounds of Formula XVI are non-radioactive, the product can be readily labeled with radioactive iodine by iodide exchange in absolute ethanol using NaI* as described above.

(XVI)+NaI*→(III)

The products are purified by conventional procedures as described above.

The compounds of Formula IV can be prepared by the following procedures. The compounds of Formula XVII are known in the art. They are diazotized by the general procedure described above to yield the diazo-compounds of Formula XVIII.

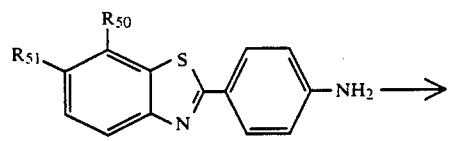

(XVII)

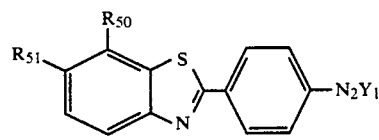

(XVIII)

In Formulas XVII and XVIII, $R_{51}$ and $R_{52}$ are as described above with respect to Formula IV, and $Y_1$ is an anion such as Cl$^-$, HSO$_4^-$, BF$_4$ or the like.

The diazo compound of Formula XVIII is then reacted with the iodobenzene compounds of Formula XIX to yield the amyloid binding diazo compounds of Formula XX.

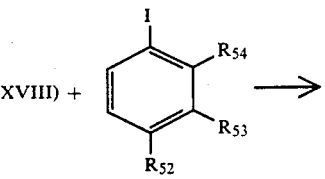

(XIX)

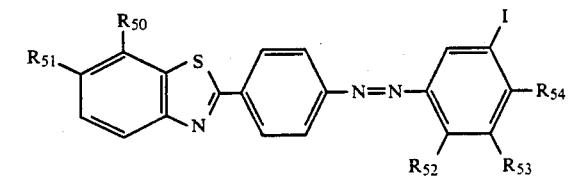

(XX)

In Formulas XIX and XX, $R_{50}$, $R_{51}$, $R_{52}$, $R_{53}$ and $R_{54}$ are as described above with respect to Formula IV.

In the above procedure, the iodine source can be radioactive iodine to directly yield the compounds of Formula IV. Alternatively, if a non-radioactive form of iodine is used and the iodine substituent of the compounds of Formula XVI are non-radioactive, the product can be readily labeled with radioactive iodine by iodide exchange in absolute ethanol using NaI* as described above.

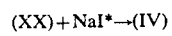

(XX)+NaI*→(IV)

The products are purified by conventional procedures as described above.

The radioactive agents can be administered by routine procedures. They can be administered orally as solids, solutions or suspensions, or injected intravenously in the form of standard aqueous solutions such as described by REMINGTON'S PHARMACEUTICAL SCIENCES. 15th Ed., Easton: Mack Publishing Co. pp 1405-1412 and 1461-1487 (1975) and THE NATIONAL FORMULARY XIV. 14th Ed. Washington: American Pharmaceutical Association (1975), the contents of which are hereby incorporated by reference. Such solutions or suspensions can contain conventional, pharmaceutically acceptable, non-toxic excipients and additives such as salts, buffers, preservatives, and the like. After sufficient time has lapsed for the reagent to reach to area of the body being examined, for example from 30 minutes to 48 hours, the area of the patient under diagnosis is examined by routine imaging techniques such as SPECT and planar scintillation imaging. The distribution of the bound radioactive isotope and its decrease with time is monitored. By comparing the results with data obtained from studies of clinically normal individuals, the presence of cranial or other site deposits of amyloid can be determined, and the diagnosis of Alzheimer's disease (cranial) or other amyloidosis thereby confirmed.

This invention is further illustrated by the following specific but non-limiting examples. Temperatures are given in degrees Centigrade and percentages as weight percents unless otherwise specified. Procedures which have been previously carried out are presented in the past tense, and procedures which are being constructively reduced to practice in this application are presented in the present tense.

EXAMPLE 1

Radioiodinated Benzo Orange R (IBOR)

Technical grade Benzo Orange R (BOR, Pfalz and Bauer) was purified by extraction with methanol and rotoevaporation to dryness, giving a 25–30% yield of red powder.

BOR (0.10 g, 0.16 mmole) was dissolved in 20 mL of anhydrous methanol giving a deep red solution. To this solution was added 0.024 g (0.16 mmole) of non-radioactive sodium iodide and 0.09 mCi of $Na^{125}I$. After all solids were dissolved, Chloramine-T tris hydrate (0.45 g, 0.16 mmole, Kodak Chemical Co.) in 1 mL of methanol was added with vigorous stirring, resulting in a dark red-brown solution. After 1 hr of stirring, the solution was rotoevaporated to dryness. The IBOR was purified by preparative RPTLC with a radiochemical yield of 12%.

Repeating this method using $Na^{123}I$ yields the radiolabeled IBOR, 4-amino-3-(4-(1-carboxy-2-hydroxy-3-$^{123}$I-5-phenyldiazo)-biphen-4'-yldiazo)-naphthalene-1-sulfonic acid.

EXAMPLE 2

Radioiodinated Benzo Orange R (IBOR)

In alternate iodination method, BOR (0.50 g, 0.82 mmol) was slurried in 50 mL of anhydrous methanol. A solution of ICl (0.14 g, 0.86 mmol) in 0.5 mL of methanol was added with vigorous stirring, resulting in a dark red-brown solution. After 1 hr of stirring, the product was isolated by rotoevaporation. Purification of the IBOR was accomplished by preparative RPTLC with a yield of 70–90%. $^1HNMR$ ($D_6$-DMSO, 250 MHz) delta 8.74(d, naphthyl-H), 8.43(d, naphthyl-H), 8.20–8.32(S,S,S, naphthyl-H, phenyl-H, phenyl-H), 8,10(d, benzidine-H), 7.89–7.99(d,d,d, benzidine-H), 7.73(S, —$NH_2$), 7.55(t,t, naphthyl-H).

This method was repeated using BOR (0.025 g, 0.041 mmol) in 2.5 mL of methanol. Addition of ICl (0.0067 g, 0.042 mmol) in 0.25 mL of methanol containing 0.20 mCi $Na^{125}I$ gave the radiolabeled product in a radiochemical yield of 32%.

Repeating this procedure but replacing $Na^{125}I$ with $Na^{123}I$ yields the corresponding $^{123}$IBOR product.

EXAMPLE 3

Radioidinated Benzo Orange R (IBOR)

In a radiolabelling by iodide exchange, IBOR (10 mg, 0.014 mmol) is slurried in 1 mL of absolute ethanol in a high pressure reaction flask fitted with a teflon cap. $Na^{125}I$, 0.1–10 mCi is added and the flask sealed. The mixture is heated to 150° C. for 6–18 hr. The product is purified by preparative RPTLC.

Repeating this procedure with $Na^{123}I$ yields the corresponding $^{123}$I labeled product.

EXAMPLE 4

Diazobiphenyl Compound, Formula VII 3,3-Dimethoxybenzidine (0.98 g, 4 mmole) was slurried in 20 mL of water containing 2 mL of 12M HCl at 0° C. Sodium nitrite (0.55 g, 8 mmole) in 5 mL water was added with stirring, yielding the chloride salt of 4,4'-bisdiazo-3,3'-dimethoxybiphenyl.

EXAMPLE 5

Diazobiphenyl Compounds, Formula VII

Repeating the procedure of Example 4, but replacing 3,3'-dimethoxybenzidine with benzidine, 3,3'-dichlorobenzidine, 3,3'-dimethylbenzidine, 2,2'-disulfobenzidine and 3,3'-dicarboxybenzidine yields the corresponding salts of 4,4'-bisdiazobiphenyl, 4,4'-bisdiazo-3,3'-dichlorobiphenyl, 4,4'-bisdiazo-3,3'dimethylbiphenyl, 4,4'-bisdiazo-2,2'-disulfobiphenyl, and 4,4'-bisdiazo-3,3'-dicarboxybiphenyl.

EXAMPLE 6

Napthalenesulfonic Acid Compounds, Formula XI

Benzidine (0.5 g, 2.7 mmol) was slurried in 20 mL of water containing 1 mL of 12M HCl at 0° C. Sodium nitrite (0.38 g, 5.4 mmol) in 5 mL of water was added with vigorous stirring, yielding the bisdiazobenzidine. The solution was diluted to 100 mL with water at 0° C. 4-Aminonaphthalene-1-sulfonic acid (0.61 g, 2.7 mmol) was dissolved in 25 mL of water by adding a minimum amount of 1M NaOH to dissolve all solids. The solution was chilled to 0° C.

The solution of the 4-aminonaphthalene-1-sulfonic acid was added dropwise to the solution of bisdiazobenzidine with concurrent dropwise addition of 1M NaOH to maintain the pH between 6 and 7. After 30 min of stirring, a solution of 2-iodophenol (0.60 g, 2.7 mmol) in 5 mL of water with enough 1M NaOH to dissolve all solids was added at once. The pH of the mixture was adjusted to pH 11 by addition of 1M NaOH and stirred for 15 min. The product was isolated by rotoevaporation and purified by column chromatography using silica gel and eluting with 85:15 v/v dichloromethane/methanol to yield 3-(4-(1-hydroxy-2-iodophen-4-yldiazo)-biphen-4'-yl-diazo)-4-aminonaphthalene-1-sulfonic acid. $^1H$ ($D_6$-DMSO/$D_2O$ 250 Mhz) delta 8.69(d, naphthyl-H), 8.37(d, naphthyl-H), 8.26(S, naphthyl-H), 8.18(S, phenyl-H), 7,86(d, benzidine-H), 7.80(d, phenyl-H), 7.73(d, benzidine-H), 7.1(t,t, naphthyl-H), 7.39(d,d, benzidine-H), 7.02(d, phenyl-H).

EXAMPLE 7

Napthalenesulfonic Acid Compounds, Formula XI

Repeating the procedure of Example 6 but replacing the 4-aminonaphthalene-1-sulfonic acid with 4-amino-5-hydroxynaphthalene-1-sulfonic acid, and 4-amino-5-hydroxynaphthalene-2,7-disulfonic acid and maintaining the pH of the first coupling reaction between 3 and 7 yields the corresponding, respective, 3-(4-(1-hydroxy-2-iodophen-4-yldiazo)-biphen-4'-yldiazo)-4-amino-5-hydroxynaphthalene-1-sulfonic acid, and 3-(4-(1-hydroxy-2-iodophen-4-yldiazo)-biphen-4'-yldiazo)-4-amino-5-hydroxynaphthalene-2,7-disulfonic acid.

EXAMPLE 8

Napthalenesulfonic Acid Compounds, Formula XI

Repeating the procedure of Example 6 but replacing the 4-aminonaphthalene-1-sulfonic acid with 4-amino-5-hydroxynaphthalene-1-sulfonic acid, 4-amino-5-hydroxynaphthalene-1,3-disulfonic acid, and 4-amino-5-hydroxynaphthalene-2,7-disulfonic acid and maintaining the pH of the first coupling reaction between 8 and 11 yields the corresponding, respective, 6-(4-(1-hydroxy-2-iodophen-4-yldiazo)-biphen-4'-yldiazo)-4-amino-5-hydroxynaphthalene-1-sulfonic acid,
6-(4-(1-hydroxy-2-iodophen-4-yldiazo)-biphen-4'-yldiazo)-4-amino-5-hydroxynaphthalene-1,3-disulfonic acid, and
6-(4-(1-hydroxy-2-iodophen-4-yldiazo)-biphen-4'-yldiazo)-4-amino-5-hydroxynaphthalene-2,7-disulfonic acid.

EXAMPLE 9

Napthalenesulfonic Acid Compounds, Formula XI

Repeating the procedure of Example 6 but replacing the benzidine with 3,3'-dimethylbenzidine, 3,3'-dimethoxybenzidine, 3,3'-dichlorobenzidine, 3,3'-dinitrobenzidine, benzidine-2,2'-disulfonic acid and benzidine-3,3'-dicarboxylic acid yields the following, respective, 3-(4-(1-hydroxy-2-iodophen-4-yldiazo)-3,3'-dimethylbiphen-4'-yldiazo)-4-aminonaphthalene-1-sulfonic acid,
3-(4-(1-hydroxy-2-iodophen-4-yldiazo)-3,3'-dimethoxybiphen-4'-yldiazo)-4-aminonaphthalene-1-sulfonic acid,
3-(4-(1-hydroxy-2-iodophen-4-yldiazo)-3,3'-dichlorobiphen-4'-yldiazo)-4-aminonaphthalene-1-sulfonic acid,
3-(4-(1-hydroxy-2-iodophen-4-yldiazo)-3,3'-dinitrobiphen-4'-yldiazo)-4-aminonaphthalene-1-sulfonic acid, and
3-(4-(1-hydroxy-2-iodophen-4-yldiazo)-2,2'-disulfobiphen-4'-yldiazo)-4-aminonaphthalene-1-sulfonic acid.

EXAMPLE 10

Napthalenesulfonic Acid Compounds, Formula XI

Repeating the procedure of Example 6 but replacing the 2-iodophenol with 4-iodophenol, 4-iodo-2-methylphenol, 4-iodo-2-methoxyphenol, 2-carboxy-4-iodophenol, 2-hydroxy-5-iodobenzoic acid, methyl 2-hydroxy-5-iodobenzoate, 2-iodo-6-methylphenol, 2-iodo-6-methoxyphenol, 2-hydroxy-3-iodobenzoic acid, methyl 2-hydroxy-3-iodobenzoate, 2-iodo-4-methylphenol, 2-iodo-4-methoxyphenol, 4-hydroxy-3-iodobenzoic acid, methyl 4-hydroxy-3-iodobenzoate, phenol, 4-methylphenol, 4-methoxyphenol, 4-hydroxybenzoic acid, methyl 4-hydroxybenzoate, 2-methylphenol, 2-methoxyphenol, 2-hydroxybenzoic acid, and methyl 2-hydroxybenzoate, yields the corresponding, respective, 3-(4-(1-hydroxy-4-iodophen-2-yldiazo)-biphen-4'-yldiazo)-4-aminoaophthalene-1-sulfonic acid,
3-(4-(1-hydroxy-4-iodo-2-methylphen-2-yldiazo)-biphen-4'-yldiazo)-4-aminonaphthalene-1-sulfonic acid,
3-(4-(1-hydroxy-4-iodo-2-methoxyphen-2-yldiazo)-biphen-4'-yldiazo)-4-aminonaphthalene-1-sulfonic acid,
3-(4-(1-carboxy-2-hydroxy-5-iodophen-3-yldiazo)-biphen-4'-yldiazo)-4-aminonaphthalene-1-sulfonic acid,
3-(4-(2-hydroxy-5-iodo-1-methyloxycarbonyl-phen-3-yldiazo)-biphen-4'-yldiazo)-4-aminonaphthalene-1-sulfonic acid,
3-(4-(1-hydroxy-2-iodo-6-methylphen-4-yldiazo)-biphen-4'-yldiazo)-4-aminonaphthalene-1-sulfonic acid,
3-(4-(1-hydroxy-2-iodo-6-methoxyphen-4-yldiazo)-biphen-4'-yldiazo)-4-aminonaphthalene-1-sulfonic acid,
3-(4-(1-carboxy-2-hydroxy-3-iodophen-5-yldiazo)-biphen-4'-yldiazo)-4-aminonaphthalene-1-sulfonic acid,
3-(4-(2-hydroxy-3-iodo-1-methyloxycarbonyl-phen-5-yldiazo)-biphen-4'-yldiazo)-4-aminonaphthalene-1-sulfonic acid,
3-(4-(1-hydroxy-2-iodo-4-methylphen-6-yldiazo)-biphen-4'-yldiazo)-4-aminonaphthalene-1-sulfonic acid,
3-(4-(1-hydroxy-2-iodo-4-methoxyphen-6-yldiazo)-biphen-4'-yldiazo)-4-aminonaphthalene-1-sulfonic acid,
3-(4-(1-carboxy-4-hydroxy-3-iodophen-5-yldiazo)-biphen-4'-yldiazo)-4-aminonaphthalene-1-sulfonic acid,
3-(4-(4-hydroxy-3-iodo-1-methyloxycarbonylphen-5yldiazo)-biphen-4'-yldiazo)-4-aminonaphthalene-1-sulfonic acid,
3-(4-(1-hydroxyphen-4-yldiazo)-biphen-4'-yldiazo)-4-aminonaphthalene-1-sulfonic acid,
3-(4-(1-hydroxy-4-methylphen-2-yldiazo)-biphen-4'-yldiazo)-4-aminonaphthalene-1-sulfonic acid,
3-(4-(1-hydroxy-4-methoxyphen-2-yldiazo)-biphen-4'-yldiazo)-4-aminonaphthalene-1-sulfonic acid,
3-(4-(1-carboxy-4-hydroxyphen-3-yldiazo)-biphen-4'-yldiazo)-4-aminonaphthalene-1-sulfonic acid,
3-(4-(4-hydroxy-1-methyloxycarbonylphen-3-yldiazo)-biphen-4'-yldiazo)-4-aminonaphthalene-1-sulfonic acid,
3-(4-(1-hydroxy-2-methylphen-4-yldiazo)-biphen-4'-yldiazo)-4-aminonaphthalene-1-sulfonic acid,
3-(4-(1-hydroxy-2-methoxyphen-4-yldiazo)-biphen-4'-yldiazo)-4-aminonaphthalene-1-sulfonic acid,
3-(4-(1-carboxy-2-hydroxyphen-5-yldiazo)-biphen-4'-yldiazo)-4-aminonaphthalene-1-sulfonic acid, and
3-(4-(2-hydroxy-1-methyloxycarbonylphen-5-yldiazo)-biphen-4'-yldiazo)-4-aminonaphthalene-1-sulfonic acid.

EXAMPLE 11

Napthalenesulfonic Acid Compounds, Formula XI

Repeating the procedure of Example 6 but replacing 2-iodophenol with N-methyl-2-iodoaniline, N,N-dimethyl-2-iodoaniline, N-methylaniline and N,N-dimethylaniline and maintaining the pH of the solution at 5–7 during the second diazo coupling yields the corresponding 3-(4-(2-iodo-1-methylaminophen-4-yldiazo)-biphen-4'-yldiazo)-4-aminonaphthalene-1-sulfonic acid,
3-(4-(2-iodo-1,1-dimethylaminophen-4-yldiazo)-biphen-4'-yldiazo)-4-aminonaphthalene-1-sulfonic acid,
3-(4-(1-methylaminophen-4-yldiazo)-biphen-4'-yldiazo)-4-aminonaphthalene-1-sulfonic acid, and
3-(4-(1,1-dimethylaminophen-4-yldiazo)-biphen-4'-yldiazo)-4-aminonaphthalene-1-sulfonic acid.

EXAMPLE 12

Napthalenesulfonic Acid Compounds, Formula XI

Repeating the procedure of Example 2 but replacing BOR with 3-(4-(1-hydroxyphen-4-yldiazo)-biphen-4'-yldiazo)-4-aminonaphthalene-1-sulfonic acid,
3-(4-(1-hydroxy-4-methylphen-2-yldiazo)-biphen-4'-yldiazo)-4-aminonaphthalene-1-sulfonic acid,
3-(4-(1-hydroxy-4-methoxyphen-2-yldiazo)-biphen-4'-yldiazo)-4-aminonaphthalene-1-sulfonic acid,
3-(4-(1-carboxy-4-hydroxyphen-3-yldiazo)-biphen-4'-yldiazo)-4-aminonaphthalene-1-sulfonic acid,
3-(4-(4-hydroxy-1-methyloxycarbonylphen-3-yldiazo)-biphen-4'-yldiazo)-4-aminonaphthalene-1-sulfonic acid,
3-(4-(1-hydroxy-2-methylphen-4-yldiazo)-biphen-4'-yldiazo)-4-aminonaphthalene-1-sulfonic acid,
3-(4-(1-hydroxy-2-methoxyphen-4-yldiazo)-biphen-4'-yldiazo)-4-aminonaphthalene-1-sulfonic acid,
3-(4-(1-carboxy-2-hydroxyphen-5-yldiazo)-biphen-4'-yldiazo)-4-aminonaphthalene-1-sulfonic acid,
3-(4-(2-hydroxy-1-methloxycarbonylphen-5-yldiazo)-biphen-4'-yldiazo)-4-aminonaphthalene-1-sulfonic acid,
3-(4-(1-methylaminophen-4-yldiazo)-biphen-4'-yldiazo)-4-aminonaphthalene-1-sulfonic acid, and
3-(4-(1,1-dimethylaminophen-4-yldiazo)-biphen-4'-yldiazo)-4-aminonaphthalene-1-sulfonic acid yields the corresponding, respective iodinated compounds,
3-(4-(1-hydroxy-2-iodophen-4-yldiazo)-biphen-4'-yldiazo)-4-aminonaphthalene-1-sulfonic acid,
3-(4-(1-hydroxy-2-iodo-4-methylphen-6-yldiazo)-biphen-4'-yldiazo)-4-aminonaphthalene-1-sulfonic acid,
3-(4-(1-hydroxy-2-iodo-4-methoxyphen-6-yldiazo)-biphen-4'-yldiazo)-4-aminonaphthalene-1-sulfonic acid,
3-(4-(1-carboxy-4-hydroxy-3-iodophen-5-yldiazo)-biphen-4'-yldiazo)-aminonaphthalene-1-sulfonic acid,
3-(4-(4-hydroxy-3-iodo-1-methyloxycarbonylphen-5-yldiazo)-biphen-4'-yldiazo)-4-aminonaphthalene-1-sulfonic acid,
3-(4-(1-hydroxy-2-iodo-6-methylphen-4-yldiazo)-biphen-4'-yldiazo)-4-aminonaphthalene-1-sulfonic acid,
3-(4-(1-hydroxy-2-iodo-6-methoxyphen-4-yldiazo)-biphen-4'-yldiazo)-4-aminonaphthalene-1-sulfonic acid,
3-(4-(1-carboxy-2-hydroxy-3-iodophen-5-yldiazo)-biphen-4'-yldiazo)-4-aminonaphthalene-1-sulfonic acid,
3-(4-(2-hydroxy-3-iodo-1-methyloxycarbonylphen-5-yldiazo)-biphen-4'-yldiazo)-4-aminonaphthalene-1-sulfonic acid,
3-(4-(2-iodo-1-methylaminophen-4-yldiazo)-biphen-4'-yldiazo)-4-aminonaphthalene-1-sulfonic acid, and
3-(4-(2-iodo-1,1-dimethylaminophen-4-yldiazo)-biphen-4'-yldiazo)-4-aminonaphthalene-1-sulfonic acid.

EXAMPLE 13

Napthalenesulfonic Acid Compounds, Formula XI

Repeating the procedure of Example 3 but replacing IBOR with the products of Examples 6 to 10 yields the corresponding, respective, $^{125}I$ and $^{123}I$ products wherein iodo(*) represents either $^{125}I$ or $^{123}I$:

3-(4-(1-hydroxy-2-iodo(*)phen-4-yldiazo)-biphen-4'-yldiazo)-4-aminonaphthalene-1-sulfonic acid.

3-(4-(1-hydroxy-2-iodo(*)phen-4-yldiazo)-biphen-4'-yldiazo)-4-amino-5-hydroxynaphthalene-1-sulfonic acid,
3-(4-(1-hydroxy-2-iodo(*)phen-4-yldiazo)-biphen-4'-yldiazo)-4-amino-5-hydroxynaphthalene-1,3-disulfonic acid,
3-(4-(1-hydroxy-2-iodo(*)phen-4-yldiazo)-biphen-4'-yldiazo)-4-amino-5-hydroxynaphthalene-2,7-disulfonic acid,
3-(4-(1-hydroxy-2-iodo(*)phen-4-yldiazo)-3,3'-dimethylbiphen-4'-yldiazo)-4-aminonaphthalene-1-sulfonic acid,
3-(4-(1-hydroxy-2-iodo(*)phen-4-yldiazo)-3,3'-dimethoxybiphen-4'-yldiazo)-4-aminonaphthalene-1-sulfonic acid,
3-(4-(1-hydroxy-2-iodo(*)phen-4-yldiazo)-3,3'-dichlorobiphen-4'-yldiazo)-4-aminonaphthalene-1-sulfonic acid,
3-(4-(1-hydroxy-2-iodo(*)phen-4-yldiazo)-3,3'-dinitrobiphen-4'-yldiazo)-4-aminonaphthalene-1-sulfonic acid,
3-(4-(1-hydroxy-2-iodo(*)phen-4-yldiazo)-2,2'-disulfobiphen-4'-yldiazo)-4-aminonaphthalene-1-sulfonic acid,
3-(4-(1-hydroxy-4-iodo(*)phen-2-yldiazo)-biphen-4'-yldiazo)-4-aminonaphthalene-1-sulfonic acid,
3-(4-(1-hydroxy-4-iodo(*)-2-methylphen-2-yldiazo)-biphen-4'-yldiazo)-4-aminonanphthalene-1-sulfonic acid,
3-(4-(1-hydroxy-4-iodo(*)-2-methoxyphen-2-yldiazo)-biphen-4'-yldiazo)-4-aminonaphthalene-1-sulfonic acid,
3-(4-(1-carboxy-2-hydroxy-5-iodo(*)phen-3-yldiazo)-biphen-4'-yldiazo)-4-aminonaphthalene-1-sulfonic acid,
3-(4-(2-hydroxy-5-iodo(*)-1-methyloxycarbonyl-phen-3-yldiazo)-biphen-4'-yldiazo)-4-aminonaphthalene-1-sulfonic acid,
3-(4-(1-hydroxy-2-iodo(*)-6-methylphen-4-yldiazo)-biphen-4'-yldiazo)-4-aminonaphthalene-1-sulfonic acid,
3-(4-(1-hydroxy-2-iodo(*)-6-methoxyphen-4-yldiazo)-biphen-4'-yldiazo)-4-aminonaphthalene-1-sulfonic acid,
3-(4-(1-carboxy-2-hydroxy-3-iodo(*)phen-5-yldiazo)-biphen-4'-yldiazo)-4-aminonaphthalene-1-sulfonic acid,
3-(4-(2-hydroxy-3-iodo(*)-1-methyloxycarbonyl-phen-5-yldiazo)-biphen-4'-yldiazo)-4-aminonaphthalene-1-sulfonic acid,
3-(4-(1-hydroxy-2-iodo(*)-4-methylphen-6-yldiazo)-biphen-4'-yldiazo)-4-aminonaphthalene-1-sulfonic acid,
3-(4-(1-hydroxy-2-iodo(*)-4-methoxyphen-6-yldiazo)-biphen-4'-yldiazo)-4-aminonaphthalene-1-sulfonic acid,
3-(4-(1-carboxy-4-hydroxy-3-iodo(*)phen-5-yldiazo)-biphen-4'-yldiazo)-4-aminonaphthalene-1-sulfonic acid,
3-(4-(4-hydroxy-3-iodo(*)-1-methyloxycarbonylphen-5-yldiazo)-biphen-4'-yldiazo)-4-aminonaphthalene-1-sulfonic acid,
3-(4-(2-iodo(*)-1-methylaminophen-4-yldiazo)-biphen-4'-yldiazo)-4-aminonaphthalene-1-sulfonic acid,
3-(4-(2-iodo(*)-1,1-dimethylaminophen-4-yldiazo)-biphen-4'-yldiazo)-4-aminonaphthalene-1-sulfonic acid, 3-(4-(1-hydroxy-2-iodo(*)phen-4-yldiazo)-biphen-4'-yldiazo)-4-aminonaphthalene-1-sulfonic acid, 3-(4-(1-hydroxy-2-iodo(*)-4-methylphen-6-yldiazo)-biphen-4'-yldiazo)-4-aminonaphthalene-1-sulfonic acid, 3-(4-(1-hydroxy-2-iodo(*)-4-methoxyphen-6-yldiazo)-biphen-4'-yldiazo)-4-aminonaphthalene-1-sulfonic acid, 3-(4-(1-carboxy-4-hydroxy-3-iodo(*)phen-5-yldiazo)-biphen-4'-yldiazo)-aminonaphthalene-1-sulfonic acid, 3-(4-(4-hydroxy-3-iodo(*)-1-methyloxycarbonylphen-5-yldiazo)-biphen-4'-yldiazo)-4-aminonaphthalene-1-sulfonic acid, 3-(4-(1-hydroxy-2-iodo(*)-6-methylphen-4-yldiazo)-biphen-4'-yldiazo)-4-aminonaphthalene-1-sulfonic acid, 3-(4-(1-hydroxy-2-iodo(*)-6-methoxyphen-4-yldiazo)-biphen-4'-yldiazo)-4-aminonaphthalene-1-sulfonic acid, 3-(4-(1-carboxy-2-hydroxy-3-iodo(*)phen-5-yldiazo)-biphen-4'-yldiazo)-4-aminonaphthalene-1-sulfonic acid, 3-(4-(2-hydroxy-3-iodo(*)-1-methyloxycarbonylphen-5-yldiazo)-biphen-4'-yldiazo)-4-aminonaphthalene-1-sulfonic acid, 3-(4-(2-iodo(*)-1-methylaminophen-4-yldiazo)-biphen-4'-yldiazo)-4-aminonaphthalene-1-sulfonic acid, and 3-(4-(2-iodo(*)-1,1-dimethylaminophen-4-yldiazo)-biphen-4'-yldiazo)-4-aminonaphthalene-1-sulfonic acid.

EXAMPLE 14

Preparation of Direct Blue 4

1.0 g (4.1 mmole) of 3,3'-dimethoxybenzidine (Aldrich Chemical Co., Milwaukee, Wis. is slurried in 20 mL of water containing 2 mL of 12M HCl at 0° C. To this mixture is added 0.56 g (8.2 mmole) of sodium nitrite, giving a red solution of bis-diazo-3,3'-dimethoxybenzidine. This solution is added with vigorous stirring to a solution of 2.0 g (8.4 mmol) 4-amino-5-hydroxynaphthalene-1-sulfonic acid in 200 mL of water adjusted to pH 10 with 1M NaOH. A deep blue color forms rapidly, and stirring is continued for 1 hr. The pH of the mixture is adjusted to 7.0, and the solvent is removed by rotoevaporation.

The product is purified by dissolving the blue solid in a minimum amount of methanol with a few drops of 1M NaOH. The solution is spotted on 20 cm×20 cm $C_{18}$ silica reverse phase TLC plates and eluted with 80:20:0.1 v/v/v methanol/water/trifluoacetic acid. The product is isolated from the silica by extraction with methanol, followed by evaporation to yield 6,6'-(3,3'-dimethoxybiphenyl-4,4'-diyl)bis(azo)bis(4-amino-5-hydroxynaphthalene-1-sulfonic acid).

EXAMPLE 15

Radioiodinated Chicago Sky Blue 6B (CSB)

0.20 g (0.20 mmole) of CSB was dissolved in 7 mL of water. Another solution containing 0.30 g (0.2 mmole) NaI, 0.056 g (0.20 mmole) Chloramine-T, and 0.20 mCi $Na^{125}I$ in 4 mL of water was added to the solution of CSB with vigorous stirring for 30 min, giving a 4–5% yield of mono-radioiodinated CBS (of Formula II).

Repeating this procedure with NaI (non-radioactive) and $Na^{123}I$ yields the corresponding monoiodinated and mono-radioiodinated CBS of Formula XIV and Formula II, 6,6'-((3,3'-dimethoxybiphen-4,4'-diyl)bis(-diazo)bis(4-amino-5-hydroxy-8-iodonaphthalene-1,3-disulfonic acid, sodium salt.

Repeating these procedures but replacing CSB with the Direct Blue 4 product of Example 12 yields the corresponding mono-radioiodinated Direct Blue 4 product.

EXAMPLE 16

Dinaphthyldiazobiphenyl compounds (Formula XIV)

Repeating the procedure of Example 14 at pH 3 to 7, but replacing 3,3'-dimethoxybenzidine with benzidine, 3,3'-dichlorobenzidine, 3,3'-dimethylbenzidine, 3,3-dicarboxybenzidine, and 2,2'-disulfobenzidine yields the corresponding, respective sodium salts of 3,3'-(biphenyl-4,4'-diyl)bis(azo)bis(4-amino-5-hydroxy-1-naphthalenesulfonic acid);

3,3'-(3,3'-dichlorobiphenyl-4,4'-diyl)bis(azo)bis(4-amino-5-hydroxy-1-naphthalenesulfonic acid);

3,3'-(3,3'-dimethylbiphenyl-4,4'-diyl)bis(azo)bis(4-amino-5-hydroxy-1-naphthalenesulfonic acid);

3,3'-(3,3'-dicarboxybiphenyl-4,4'-diyl)bis(azo)bis(4-amino-5-hydroxy-1-naphthalenesulfonic acid); and 3,3'-(2,2'-disulfobiphenyl-4,4'-diyl)bis(azo)bis(4-amino-5-hydroxy-1-naphthalenesulfonic acid).

Repeating the above procedure at pH 10 yields the corresponding sodium salts of 6,6'-(biphenyl-4,4'-diyl)bis(azo)bis(4-amino-5-hydroxy-1-naphthalenesulfonic acid);

6,6'-(3,3'-dichlorobiphenyl-4,4'-diyl)bis(azo)bis(4-amino-5-hydroxy-1-naphthalenesulfonic acid);

6,6'-(3,3'-dimethylbiphenyl-4,4'-diyl)bis(azo)bis(4-amino-5-hydroxy-1-naphthalenesulfonic acid);

6,6'-(3,3'-dicarboxybiphenyl-4,4'-diyl)bis(azo)bis(4-amino-5-hydroxy-1-naphthalenesulfonic acid); and 6,6'-(2,2'-disulfobiphenyl-4,4'-diyl)bis(azo)bis(4-amino-5-hydroxy-1-naphthalenesulfonic acid).

EXAMPLE 17

Iodinated Dinaphthyldiazobiphenyl Compounds (Formulas II and XIV)

Repeating the procedure of Example 15, but replacing the Chicago Sky Blue with the products of Example 16 yields the corresponding respective iodine and radiolabeled $^{123}I$ and $^{125}I$ substituted 3,3'-(biphenyl-4,4'-diyl)bis(azo)bis(4-amino-6-iodo-5-hydroxy-1-naphthalenesulfonic acid);

3,3'-(3,3'-dichlorobiphenyl-4,4'-diyl)bis(azo)bis(4-amino-6-iodo-5-hydroxy-1-naphthalenesulfonic acid);

3,3'-(3,3'-dimethylbiphenyl-4,4'-diyl)bis(azo)bis(4-amino-6-iodo-5-hydroxy-1-naphthalenesulfonic acid);

3,3'-(3,3'-dicarboxybiphenyl-4,4'-diyl)bis(azo)bis(4-amino-6-iodo-5-hydroxy-1-naphthalenesulfonic acid);

3,3'-(2,2'-disulfobiphenyl-4,4'-diyl)bis(azo)bis(4-amino-6-iodo-5-hydroxy-1-naphthalenesulfonic acid);

3,3'-(biphenyl-4,4'-diyl)bis(azo)bis(4-amino-8-iodo-5-hydroxy-1-naphthalenesulfonic acid);

3,3'-(3,3'-dichlorobiphenyl-4,4'-diyl)bis(azo)bis(4-amino-8-iodo-5-hydroxy-1-naphthalenesulfonic acid);

3,3'-(3,3'-dimethylbiphenyl-4,4'-diyl)bis(azo)bis(4-amino-8-iodo-5-hydroxy-1-naphthalenesulfonic acid);

3,3'-(3,3'-dicarboxybiphenyl-4,4'-diyl)bis(azo)bis(4-amino-8-iodo-5-hydroxy-1-naphthalenesulfonic acid);

3,3'-(2,2'-disulfobiphenyl-4,4'-diyl)bis(azo)bis(4-amino-8-iodo-5-hydroxy-1-naphthalenesulfonic acid);
6,6'-(biphenyl-4,4'-diyl)bis(azo)bis(4-amino-8-iodo-5-hydroxy-1-naphthalenesulfonic acid);
6,6'-(3,3'-dichlorobiphenyl-4,4'-diyl)bis(azo)bis(4-amino-8-iodo-5-hydroxy-1-naphthalenesulfonic acid);
6,6'-(3,3'-dimethylbiphenyl-4,4'-diyl)bis(azo)bis(4-amino-8-iodo-5-hydroxy-1-naphthalenesulfonic acid);
6,6'-(3,3'-dicarboxybiphenyl-4,4'-diyl)bis(azo)bis(4-amino-8-iodo-5-hydroxy-1-naphthalenesulfonic acid); and
6,6'-(2,2'-disulfobiphenyl-4,4'-diyl)bis(azo)bis(4-amino-8-iodo-5-hydroxy-1-naphthalenesulfonic acid).

EXAMPLE 18

Iodinated Dinaphthyldiazobiphenyl Compounds
(Formulas II and XIV)

Chicago Sky Blue 6B (0.85 g, 0.086 mmol) is slurried in 5 mL of anhydrous methanol. A solution of 0.14 g (0.086 mmole) of ICl (Aldrich) in 1 ml of methanol is added with vigorous stirring. After one hour of stirring, the product is isolated by rotoevaporation. Purification of the product is accomplished by preparative RPTLC to yield the iodinated Chicago Sky Blue, a compound of Formula XIV.

Repeating the procedure but replacing the ICl with $^{123}$ICl yields the corresponding radiodinated Chicago Sky Blue, a compound of Formula II.

Repeating the above procedure, but replacing the Chicago Sky Blue with the products of Example 14 yields the corresponding respective iodine and radiolabeled $^{123}$I and $^{125}$I substituted 3,3'-(biphenyl-4,4'-diyl)bis(azo)bis(4-amino-6-iodo-5-hydroxy-1-naphthalenesulfonic acid);
3,3'-(3,3'-dichlorobiphenyl-4,4'-diyl)bis(azo)bis(4-amino-6-iodo-5-hydroxy-1-naphthalenesulfonic acid);
3,3'-(3,3'-dimethylbiphenyl-4,4'-diyl)bis(azo)bis(4-amino-6-iodo-5-hydroxy-1-naphthalenesulfonic acid);
3,3'-(3,3'-dicarboxybiphenyl-4,4'-diyl)bis(azo)bis(4-amino-6-iodo-5-hydroxy-1-naphthalenesulfonic acid);
3,3'-(2,2'-disulfobiphenyl-4,4'-diyl)bis(azo)bis(4-amino-6-iodo-5-hydroxy-1-naphthalenesulfonic acid);
3,3'-(biphenyl-4,4'-diyl)bis(azo)bis(4-amino-8-iodo-5-hydroxy-1-naphthalenesulfonic acid);
3,3'-(3,3'-dichlorobiphenyl-4,4'-diyl)bis(azo)bis(4-amino-8-iodo-5-hydroxy-1-naphthalenesulfonic acid);
3,3'-(3,3'-dimethylbiphenyl-4,4'-diyl)bis(azo)bis(4-amino-8-iodo-5-hydroxy-1-naphthalenesulfonic acid);
3,3'-(3,3'-dicarboxybiphenyl-4,4'-diyl)bis(azo)bis(4-amino-8-iodo-5-hydroxy-1-napthalenesulfonic acid);
3,3'-(2,2'-disulfobiphenyl-4,4'-diyl)bis(azo)bis(4-amino-8-iodo-5-hydroxy-1-naphthalenesulfonic acid);
6,6'-(biphenyl-4,4'-diyl)bis(azo)bis(4-amino-8-iodo-5-hydroxy-1-naphthalenesulfonic acid);
6,6'-(3,3'-dichlorobiphenyl-4,4'-diyl)bis(azo)bis(4-amino-8-iodo-5-hydroxy-1-naphthalenesulfonic acid);
6,6'-(3,3'-dimethylbiphenyl-4,4'-diyl)bis(azo)bis(4-amino-8-iodo-5-hydroxy-1-naphthalenesulfonic acid);
6,6'-(3,3'-dicarboxybiphenyl-4,4'-diyl)bis(azo)bis(4-amino-8-iodo-5-hydroxy-1-naphthalenesulfonic acid); and
6,6'-(2,2'-disulfobiphenyl-4,4'-diyl)bis(azo)bis(4-amino-8-iodo-5-hydroxy-1-naphthalenesulfonic acid).

EXAMPLE 19

Radioiodinated Dinaphthyldiazobiphenyl Compounds
(Formula II)

The iodinated Chicago Sky Blue 6B product of Example 15 (substituted with non-radioactive iodine) 0.992 mg (0.1 mmole) is stirred in 1 mL of absolute ethanol in a high pressure reaction flask fitted with a teflon cap. Na$^{123}$I, 0.2–10 mCi is added, and the flask is sealed. The mixture is heated to 150° C. for 6–18 hr. The product is purified by preparative RPTLC or HPLC to yield the radioiodine substituted CSB product of Formula II.

Repeating this procedure but substituting the iodinated CSB with products of non-radioactive iodine substituted products of Example 14 yields the corresponding radioiodine substituted 3,3'-(biphenyl-4,4'-diyl)bis(azo)bis(4-amino-6-iodo-5-hydroxy-1-naphthalenesulfonic acid);
3,3'-(3,3'-dichlorobiphenyl-4,4'-diyl)bis(azo)bis(4-amino-6-iodo-5-hydroxy-1-naphthalenesulfonic acid);
3,3'-(3,3'-dimethylbiphenyl-4,4'-diyl)bis(azo)bis(4-amino-6-iodo-5-hydroxy-1-naphthalenesulfonic acid);
3,3'-(3,3'-dicarboxybiphenyl-4,4'-diyl)bis(azo)bis(4-amino-6-iodo-5-hydroxy-1-naphthalenesulfonic acid);
3,3'-(2,2'-disulfobiphenyl-4,4'-diyl)bis(azo)bis(4-amino-6-iodo-5-hydroxy-1-naphthalenesulfonic acid);
3,3'-(biphenyl-4,4'-diyl)bis(azo)bis(4-amino-8-iodo-5-hydroxy-1-naphthalenesulfonic acid);
3,3'-(3,3'-dichlorobiphenyl-4,4'-diyl)bis(azo)bis(4-amino-8-iodo-5-hydroxy-1-naphthalenesulfonic acid);
3,3'-(3,3'-dimethylbiphenyl-4,4'-diyl)bis(azo)bis(4-amino-8-iodo-5-hydroxy-1-naphthalenesulfonic acid);
3,3'-(3,3'-dicarboxybiphenyl-4,4'-diyl)bis(azo)bis(4-amino-8-iodo-5-hydroxy-1-naphthalenesulfonic acid);
3,3'-(2,2'-disulfobiphenyl-4,4'-diyl)bis(azo)bis(4-amino-8-iodo-5-hydroxy-1-naphthalenesulfonic acid);
6,6'-(biphenyl-4,4'-diyl)bis(azo)bis(4-amino-8-iodo-5-hydroxy-1-naphthalenesulfonic acid);
6,6'-(3,3'-dichlorobiphenyl-4,4'-diyl)bis(azo)bis(4-amino-8-iodo-5-hydroxy-1-naphthalenesulfonic acid);
6,6'-(3,3'-dimethylbiphenyl-4,4'-diyl)bis(azo)bis(4-amino-8-iodo-5-hydroxy-1-naphthalenesulfonic acid);
6,6'-(3,3'-dicarboxybiphenyl-4,4'-diyl)bis(azo)bis(4-amino-8-iodo-5-hydroxy-1-naphthalenesulfonic acid); and
6,6'-(2,2'-disulfobiphenyl-4,4'-diyl)bis(azo)bis(4-amino-8-iodo-5-hydroxy-1-naphthalenesulfonic acid).

EXAMPLE 20

Amino-3-(4-iodophenylazo)-naphthylenesulfonic acids
Formula XVI

4-Iodoaniline (5 g, 22.8 mmole) was dissolved in 100 mL of THF and chilled to −5° C. 5 mL (40.6 mmole) of boron trifluoride etherate was added with stirring, followed by 4 mL (33.6 mmole) of t-butylnitrite. Stirring at −5° C. was continued for 45 min. A white crystalline solid was collected by filtration and rinsed with 20 mL of THF and 2 mL portions of diethyl ether. The resulting tetrafluoroborate salt of diazo-4-iodobenzene was dried in vacuo to give a yield of 88%.

Diazo-4-iodobenzene (2.0 g, 6.3 mmole) was dissolved in 10 mL of acetonitrile. 4-Aminonaphthalene-1-sulfonic acid, sodium salt dihydrate (1.85 g, 6.6 mmole), and sodium bicarbonate (0.55 g, 6.5 mmole) were dissolved together in 25 mL of water and then diluted to 100 mL with methanol. The two solutions were combined with vigorous stirring, giving an orange-red solution. After 1 hr of stirring, the solution volume was reduced to 20 mL by rotoevaporation. The resulting red precipitate was collected by filtration and rinsed with 20 mL of acetonitrile. The product is dried in vacuo to give a 74% yield of 4-amino-3-(1-iodo-phen-4-yldiazo)-naphthylene-1-sulfonic acid. Further purification was accomplished by preparative RPTLC. $^1$H NMR (D$_6$-DMSO/D$_2$O, 250 Mhz) delta 8.69(d, naphthyl-H), 8.39(d, naphthyl-H), 8.26(S, naphthyl-H), 7.86(d, phenyl-H), 7.75(d, phenyl-H), 7.58(t, naphthyl-H), 7.51(t, naphthyl-H).

EXAMPLE 21

3-(4-iodophenylazo)-naphthylenesulfonic acids Formula XVI

Repeating the procedure of Example 20 but replacing 4-aminonapthalene-1-sulfonic acid with 4-amino-5-hydroxynaphthylene-1-sulfonic acid; 4-amino-5-hydroxynaphthalene-1,3-disulfonic acid; and 1-amino-8-hydroxynaphthylene-3,6-disulfonic acid yields the corresponding, respective 4-amino-5-hydroxy-3-(1-iodophen-4-yldiazo)-naphthylene-1-sulfonic acid;
4-amino-5-hydroxy-6-(1-iodophen-4-yldiazo)-naphthylene-1-sulfonic acid;
4-amino-5-hydroxy-6-(1-iodophen-4-yldiazo)-naphthylene-1,3-disulfonic acid;
4-amino-5-hydroxy-7-(1-iodophen-4-yldiazo)-naphthylene-2,7-disulfonic acid; and
4-amino-5-hydroxy-2-(1-iodophen-4-yldiazo)-naphthylene-2,7-disulfonic acid.

EXAMPLE 22

Substituted Naphthylene-1-sulfonic acids Formula XVI

Repeating the procedure of Example 20 but replacing 4-iodoaniline with 2-iodoaniline, 3-iodoaniline, 2-amino-4-iodotoluene, 2-amino-5-iodotoluene, 4-amino-2-iodotoluene, and 2-amino-4-iodobenzoic acid yields the corresponding, respective, 4-amino-3-(1-iodophen-2-yldiazo)-naphthylene-1-sulfonic acid,
4-amino-3-(1-iodophen-3-yldiazo)-naphthylene-1-sulfonic acid,
4-amino-3-(1-iodo-4-methylphen-3-yldiazo)-naphthylene-1-sulfonic acid,
4-amino-3-(1-iodo-3-methylphen-4-yldiazo)-naphthylene-1-sulfonic acid, and
4-amino-3-(1-carboxy-3-iodophen-2-yldiazo)-naphthylene-1-sulfonic acid.

EXAMPLE 23

3-(4-iodo(*)-phenylazo)-naphthylenesulfonic acids Formula III

10 Mg of the product of Example 20 and Na$^{125}$I were slurried in 1 mL of absolute ethanol in a high pressure flask fitted with a teflon cap. The mixture was heated to 150° C. for 18 hr, giving a radiochemical yield of 70%. The labeled dye was purified by RPTLC to yield 4-amino-3-(4-$^{125}$I-phenyldiazo)-naphthylene-1-sulfonic acid.

Repeating this procedure with Na$^{123}$I yields the corresponding 4-amino-3-(4-$^{123}$I-phenyldiazo)-naphthylene-1-sulfonic acid.

EXAMPLE 24

(iodo(*)-phenylazo)-naphthylenesulfonic acids Formula III

Repeating the procedure of Example 22 with the products of Examples 20 and 21 yields the corresponding, respective, $^{125}$I and $^{123}$I products wherein iodo(*) represents either $^{125}$I or $^{123}$I:

4-amino-5-hydroxy-3-(1-iodo(*)-phen-4-yldiazo)-naphthylene-1-sulfonic acid;
4-amino-5-hydroxy-6-(1-iodo(*)-phen-4-yldiazo)-naphthylene-1-sulfonic acid;
4-amino-5-hydroxy-6-(1-iodo(*)-phen-4-yldiazo)-naphthylene-1,3-disulfonic acid;
1-amino-8-hydroxy-7-(1-iodo(*)-phen-4-yldiazo)-naphthylene-3,6-disulfonic acid;
1-amino-8-hydroxy-2-(1-iodo(*)-phen-4-yldiazo)-naphthylene-3,6-disulfonic acid;
4-amino-3-(1-iodo(*)-phen-2-yldiazo)-naphthylene-1-sulfonic acid,
4-amino-3-(1-iodo(*)-phen-3-yldiazo)-naphthylene-1-sulfonic acid,
4-amino-3-(1-iodo(*)-phen-4-yldiazo)-naphthylene-1-sulfonic acid,
4-amino-3-(1-iodo(*)-4-methylphen-3-yldiazo)-naphthylene-1-sulfonic acid,
4-amino-3-(1-iodo(*)-3-methylphen-4-yldiazo)-naphthylene-1-sulfonic acid, and
4-amino-3-(1-carboxy-3-iodo(*)-phen-2-yldiazo)-naphthylene-1-sulfonic acid.

EXAMPLE 25

2-(4-diazophenyl)-6-methylbenzothiazole-7-sulfonic acid Formula XVIII 2-(4-Aminophenyl)-6-methylbenzothiazole-7-sulfonic acid (2.0 g, 6.2 mmole) was dissolved in 60 mL of water at pH 6.0 and chilled to 0° C. in an ice/ethanol bath. Sodium nitrite (0.51 g, 7.4 mmole) in 5 mL of water was added with stirring. 3.0 ML of 12M hydrochloric acid (36 mmole) was added with vigorous stirring, yielding an orange-yellow precipitate of the diazonium salt, 2-(4-diazophenyl)-6-methylbenzothiazole-7-sulfonic acid, sodium salt. The product is preferably used within 10 min of preparation.

EXAMPLE 26

2-(4-diazophenyl)-6-methylbenzothiazole Formula XVIII 2-(4-Aminophenyl)-6-methylbenzothiazole (10.0 g, 41.6 mmole) was dissolved in 200 mL of anhydrous THF and chilled to −15° C. under a nitrogen atmosphere. Boron trifluoride etherate (15 mL, 122 mmole) was added with stirring to give a homogenous solution. T-butyl nitrite (7.5 ml, 63 mmole) was added to the solution, and the mixture was stirred for 1 hr. A yellow precipitate was collected by filtration and rinsed with 75 mL of ether. After drying in vacuo, a 94% yield of the diazonium salt, 2-(4-diazophenyl)-6-methylbenzothiazole, boron tetrafluoride salt was obtained.

EXAMPLE 27

2-(4-diazophenyl)-benzothiazole-6-carboxylic acid Formula XVIII

Repeating the procedure of Example 25 but replacing 2-(4-aminophenyl)-6-methylbenzothiazole-7-sulfonic acid with 2-(4-aminophenyl)-6-carboxybenzothiazole yields the corresponding salt of 2-(4-diazophenyl)-benzothiazole-6-carboxylic acid.

EXAMPLE 28

2-(4-(1-hydroxy-2-iodophen-4-yldiazo)-phenyl)-6-methylbenzothiazole-7-sulfonic acid, Formula XX The product of Example 24 (6.2 mmole) was added to a solution of 1.54 g (7.0 mmole) of 2-iodophenol in 100 mL of solvent (water or 1:1 water:acetonitrile) containing 14 mmole of sodium hydroxide. The solution was stirred at 21° C. for 2 hr maintained at pH 11 and then was acidified to pH 7.0. The solvent was removed by rotoevaporation, and the remaining solid was washed with acetonitrile, collected by filtration and dried in vacuo yielding 60-85% of 2-(4-(1-hydroxy-2-iodophen-4-yldiazo)-phenyl)-6-methylbenzothiazole-7-sulfonic acid. The product was purified by reverse phase TLC to give purities of above 99%. $^1$H NMR (D$_4$-Methanol/NaOD, 250 MHz) delta 7.59 (S, Ar-H), 7.48, 7.26, 7.17, 7.04, 7.00, 6.76, 5.96(d,d,d,d,d,d,d, Ar-H), 2.13(S, CH$_3$-).

EXAMPLE 29

2-(4-(phenyldiazo)-phenyl)-benzothiazoles Formula XX

Repeating the procedure of Example 28 but replacing 2-iodophenol with 4-iodophenol, 4-iodo-2-methylphenol, 4-iodo-2-methoxyphenol, 2-carboxy-4-iodophenol, 2-hydroxy-5-iodobenzoic acid, methyl 2-hydroxy-5-iodobenzoate, 2-iodo-6-methylphenol, 2-iodo-6-methoxyphenol, 2-hydroxy-3-iodobenzoic acid, methyl 2-hydroxy-3-iodobenzoate, 2-iodo-4-methylphenol, 2-iodo-4-methoxyphenol, 4-hydroxy-3-iodobenzoic acid, methyl 4-hydroxy-3-iodobenzoate, phenol, 4-methylphenol, 4-methoxyphenol, 4-hydroxybenzoic acid, methyl 4-hydroxybenzoate, 2-methylphenol, 2-methoxyphenol, 2-hydroxybenzoic acid and methyl 2-hydroxybenzoate yields the corresponding, respective, 2-(4-(1-hydroxy-4-iodophen-2-yldiazo)-phenyl)-6-methylbenzothiazole-7-sulfonic acid,
2-(4-(1-hydroxy-4-iodo-2-methyl-6-phenyldiazo)-phenyl)-6-methylbenzothiazole-7-sulfonic acid,
2-(4-(1-hydroxy-4-iodo-2-methoxy-6-phenyldiazo)-phenyl)-6-methylbenzothiazole-7-sulfonic acid,
2-(4-(1-carboxy-2-hydroxy-5-iodo-3-phenyldiazo)-phenyl)-6-methylbenzothiazole-7-sulfonic acid,
2-(4-(2-hydroxy-5-iodo-1-methoxycarbonyl-3-phenyldiazo)-phenyl)-6-methylbenzothiazole-7-sulfonic acid,
2-(4-(1-hydroxy-2-iodo-6-methyl-4-phenyldiazo)-phenyl)-6-methylbenzothiazole-7-sulfonic acid,
2-(4-(1-hydroxy-2-iodo-6-methoxy-4-phenyldiazo)-phenyl)-6-methylbenzothiazole-7-sulfonic acid,
2-(4-(1-carboxy-2-hydroxy-3-iodo-5-phenyldiazo)-phenyl)-6-methylbenzothiazole-7-sulfonic acid,
2-(4-(2-hydroxy-3-iodo-1-methoxycarbonyl-5-phenyldiazo)-phenyl)-6-methylbenzothiazole-7-sulfonic acid,
2-(4-(1-hydroxy-2-iodo-4-methyl-6-phenyldiazo)-phenyl)-6-methylbenzothiazole-7-sulfonic acid,
2-(4-(1-hydroxy-2-iodo-4-methoxy-6-phenyldiazo)-phenyl)-6-methylbenzothiazole-7-sulfonic acid,
2-(4-(1-carboxy-4-hydroxy-3-iodo-5-phenyldiazo)-phenyl)-6-methylbenzothiazole-7-sulfonic acid,
2-(4-(4-hydroxy-3-iodo-1-methoxycarbonyl-5-phenyldiazo)-phenyl)-6-methylbenzothiazole-7-sulfonic acid,
2-(4-(1-hydroxy-4-phenyldiazo)-phenyl)-6-methylbenzothiazole-7-sulfonic acid,
2-(4-(1-hydroxy-4-methyl-2-phenyldiazo)-phenyl)-6-methylbenzothiazole-7-sulfonic acid,
2-(4-(1-hydroxy-4-methoxy-2-phenyldiazo)-phenyl)-6-methylbenzothiazole-7-sulfonic acid,
2-(4-(1-carboxy-4-hydroxy-3-phenyldiazo)-phenyl)-6-methylbenzothiazole-7-sulfonic acid,
2-(4-(4-hydroxy-1-methoxycarbonyl-3-phenyldiazo)-phenyl)-6-methylbenzothiazole-7-sulfonic acid,
2-(4-(1-hydroxy-2-methyl-4-phenyldiazo)-phenyl)-6-methylbenzothiazole-7-sulfonic acid,
2-(4-(1-hydroxy-2-methoxy-4-phenyldiazo)-phenyl)-6-methylbenzothiazole-7-sulfonic acid,
2-(4-(1-carboxy-2-hydroxy-5-phenyldiazo)-phenyl)-6-methylbenzothiazole-7-sulfonic acid, and
2-(4-(2-hydroxy-1-methoxycarbonyl-5-phenyldiazo)-phenyl)-6-methylbenzothiazole-7-sulfonic acid.

EXAMPLE 30

2-(4-(phenyldiazo)-phenyl)-benzothiazoles Formula XX

Repeating the procedure of Example 28 but replacing the 2-iodophenol with N-methyl-2-iodoaniline, N,N-dimethyl-2-iodoaniline, N-methylaniline and N,N-dimethylaniline and maintaining the solution at pH 5 to 7 yields the corresponding 2-(4-(2-iodo-1-methylamino-4-phenyldiazo)-phenyl)-6-methylbenzothiazole-7-sulfonic acid,
2-(4-(1-dimethylamino-2-iodo-4-phenyldiazo)-phenyl)-6-methylbenzothiazole-7-sulfonic acid,
2-(4-(1-methylamino-4-phenyldiazo)-phenyl)-6-methylbenzothiazole-7-sulfonic acid, and
2-(4-(1-dimethylamino-4-phenyldiazo)-phenyl)-6-methylbenzothiazole-7-sulfonic acid.

EXAMPLE 31

2-(4-(phenyldiazo)-phenyl)-benzothiazolecarboxylic acids Formula XX

Repeating the procedure of Example 28 but replacing the product of Example 25 with the products of Example 27, and replacing 2-iodophenol with 4-iodophenol, 4-iodo-2-methylphenol, 4-iodo-2-methoxyphenol, 2-carboxy-4-iodophenol, 2-hydroxy-5-iodobenzoic acid, methyl 2-hydroxy-5-iodobenzoate, 2-iodo-6-methylphenol, 2-iodo-6-methoxyphenol, 2-hydroxy-3-iodobenzoic acid, methyl 2-hydroxy-3-iodobenzoate, 2-iodo-4-methylphenol, 2-iodo-4-methoxyphenol, 4-hydroxy-3-iodobenzoic acid, methyl 4-hydroxy-3-iodobenzoate, phenol, 4-methylphenol, 4-methoxyphenol, 4-hydroxybenzoic acid, methyl 4-hydroxybenzoate, 2-methylphenol, 2-methoxyphenol, 2-hydroxybenzoic acid, methyl 2-hydroxybenzoate, yields the corresponding, respective, 2-(4-(1-hydroxy-4-iodophen-2-yldiazo)-phenyl)-6-methylbenzothiazole-6-carboxylic acid,
2-(4-(1-hydroxy-4-iodo-2-methyl-6-phenyldiazo)-phenyl)-6-methylbenzothiazole-6-carboxylic acid,
2-(4-(1-hydroxy-4-iodo-2-methoxy-6-phenyldiazo)-phenyl)-6-methylbenzothiazole-6-carboxylic acid,
2-(4-(1-carboxy-2-hydroxy-5-iodo-3-phenyldiazo)-phenyl)-6-methylbenzothiazole-6-carboxylic acid, 2-(4-(2-hydroxy-5-iodo-1-methoxycarbonyl-3-phenyldiazo)-phenyl)-6-methylbenzothiazole-6-carboxylic acid;
2-(4-(1-hydroxy-2-iodo-6-methyl-4-phenyldiazo)-phenyl)-6-methylbenzothiazole-6-carboxylic acid,
2-(4-(1-hydroxy-2-iodo-6-methoxy-4-phenyldiazo)-phenyl)-6-methylbenzothiazole-6-carboxylic acid,
2-(4-(1-carboxy-2-hydroxy-3-iodo-5-phenyldiazo)-phenyl)-6-methylbenzothiazole-6-carboxylic acid,
2-(4-(2-hydroxy-3-iodo-1-methoxycarbonyl-5-phenyldiazo)-phenyl)-6-methylbenzothiazole-6-carboxylic acid,
2-(4-(1-hydroxy-2-iodo-4-methyl-6-phenyldiazo)-phenyl)-6-methylbenzothiazole-6-carboxylic acid,
2-(4-(1-hydroxy-2-iodo-4-methoxy-6-phenyldiazo)-phenyl)-6-methylbenzothiazole-6-carboxylic acid,
2-(4-(1-carboxy-4-hydroxy-3-iodo-5-phenyldiazo)-phenyl)-6-methylbenzothiazole-6-carboxylic acid,
2-(4-(4-hydroxy-3-iodo-1-methoxycarbonyl-5-phenyldiazo)-phenyl)-6-methylbenzothiazole-6-carboxylic acid,
2-(4-(1-hydroxy-4-phenyldiazo)-phenyl-6-methylbenzothiazole-6-carboxylic acid,
2-(4-(1-hydroxy-4-methyl-2-phenyldiazo)-phenyl)-6-methylbenzothiazole-6-carboxylic acid,
2-(4-(1-hydroxy-4-methoxy-2-phenyldiazo)-phenyl)-6-methylbenzothiazole-6-carboxylic acid,
2-(4-(1-carboxy-4-hydroxy-3-phenyldiazo)-phenyl)-6-methylbenzothiazole-6-carboxylic acid,
2-(4-(4-hydroxy-1-methoxycarbonyl-3-phenyldiazo)-phenyl)-6-methylbenzothiazole-6-carboxylic acid,
2-(4-(1-hydroxy-2-methyl-4-phenyldiazo)-phenyl)-6-methylbenzothiazole-6-carboxylic acid,
2-(4-(1-hydroxy-2-methoxy-4-phenyldiazo)-phenyl)-6-methylbenzothiazole-6-carboxylic acid,
2-(4-(1-carboxy-2-hydroxy-5-phenyldiazo)-phenyl)-6-methylbenzothiazole-6-carboxylic acid, and
2-(4-(2-hydroxy-1-methoxycarbonyl-5-phenyldiazo)-phenyl)-6-methylbenzothiazole-6-carboxylic acid.

EXAMPLE 32

2-(4-(phenyldiazo)-phenyl)-benzothiazolecarboxylic acids Formula XX

Repeating the procedure of Example 28 but replacing the product of Example 25 with the products of Example 27, and replacing 2-iodophenol with N-methyl-2-iodoaniline, N,N-dimethyl-2-iodoaniline, N-methylaniline and N,N-dimethylaniline and without adding sodium hydroxide (thus maintaining the solution pH within the range of 5 to 7) yields the corresponding 2-(4-(2-iodo-1-methylamino-4-phenyldiazo)-phenyl)-6-methylbenzothiazole-6-carboxylic acid,
2-(4-(1-dimethylamino-2-iodo-4-phenyldiazo)-phenyl)-6-methylbenzothiazole-6-carboxylic acid,
2-(4-(1-methylamino-4-phenyldiazo)-phenyl)-6-methylbenzothiazole-6-carboxylic acid, and
2-(4-(1-dimethylamino-4-phenyldiazo)-phenyl)-6-methylbenzothiazole-6-carboxylic acid.

EXAMPLE 33

2-(4-(phenyldiazo)-phenyl)-benzothiazoles Formula XX

2-Iodophenol (2.6 g, 11.8 mmol) was dissolved in 200 mL of 1:1 acetonitrile/water containing 14 mL of 1M sodium hydroxide. 2-(4-Diazophenyl)-6-methylbenzothiazole (4.07 g, 12.0 mmol) was added as a solid with vigorous stirring. After 12–18 hr of stirring, the azo dye was precipitated with 1 mL of glacial acetic acid followed by rinsing with ethanol and diethylether. The dye was dried in vacuo. Purification of the dye was accomplished by NPTLC eluted with 90:10 dichloromethane:methanol to yield 2-(4-(1-hydroxy-2-iodophen-4-yldiazo)-phenyl)-6-methylbenzothiazole.

$^1$H NMR (D$_6$-DMSO, 400 MHz) delta 8.27(S, Ar-H), 8.24(d, Ar-H), 7.97(d,d, Ar-H), 7.95(S, Ar-H), 7.88(d, Ar-H), 7.38(d, Ar-H), 7.08(d, Ar-H), 2.46(S, Ar-CH$_3$).

EXAMPLE 34

2-(4-(phenyldiazo)-phenyl)-benzothiazoles Formula XX

Repeating the procedure of Example 33 but replacing 2-iodophenol with 4-iodophenol, 4-iodo-2-methylphenol, 4-iodo-2-methoxyphenol, 2-carboxy-4-iodophenol, 2-hydroxy-5-iodobenzoic acid, methyl 2-hydroxy-5-iodobenzoate, 2-iodo-6-methylphenol, 2-iodo-6-methoxyphenol, 2-hydroxy-3-iodobenzoic acid, methyl 2-hydroxy-3-iodobenzoate, 2-iodo-4-methylphenol, 2-iodo-4-methoxyphenol, 4-hydroxy-3-iodobenzoic acid, methyl 4-hydroxy-3-iodobenzoate, phenol, 4-methylphenol, 4-methoxyphenol, 4-hydroxybenzoic acid, methyl 4-hydroxybenzoate, 2-methylphenol, 2-methoxyphenol, 2-hydroxybenzoic acid and methyl 2-hydroxybenzoate, yields the corresponding, respective, 2-(4-(1-hydroxy-4-iodophen-2-yldiazo)-phenyl)-6-methylbenzothiazole,
2-(4-(1-hydroxy-4-iodo-2-methyl-6-phenyldiazo)-phenyl)-6-methylbenzothiazole,
2-(4-(1-hydroxy-4-iodo-2-methoxy-6-phenyldiazo)-phenyl)-6-methylbenzothiazole,
2-(4-(1-carboxy-2-hydroxy-5-iodo-3-phenyldiazo)-phenyl)-6-methylbenzothiazole,
2-(4-(2-hydroxy-5-iodo-1-methoxycarbonyl-3-phenyldiazo)-phenyl)-6-methylbenzothiazole,
2-(4-(1-hydroxy-2-iodo-6-methyl-4-phenyldiazo)-phenyl)-6-methylbenzothiazole,
2-(4-(1-hydroxy-2-iodo-6-methoxy-4-phenyldiazo)-phenyl)-6-methylbenzothiazole,
2-(4-(1-carboxy-2-hydroxy-3-iodo-5-phenyldiazo)-phenyl)-6-methylbenzothiazole,
2-(4-(2-hydroxy-3-iodo-1-methoxycarbonyl-5-phenyldiazo)-phenyl)-6-methylbenzothiazole,
2-(4-(1-hydroxy-2-iodo-4-methyl-6-phenyldiazo)-phenyl)-6-methylbenzothiazole,
2-(4-(1-hydroxy-2-iodo-4-methoxy-6-phenyldiazo)-phenyl)-6-methylbenzothiazole,
2-(4-(1-carboxy-4-hydroxy-3-iodo-5-phenyldiazo)-phenyl)-6-methylbenzothiazole,
2-(4-(4-hydroxy-3-iodo-1-methoxycarbonyl-5-phenyldiazo)-phenyl)-6-methylbenzothiazole,
2-(4-(1-hydroxy-4-phenyldiazo)-phenyl)-6-methylbenzothiazole,
2-(4-(1-hydroxy-4-methyl-2-phenyldiazo)-phenyl)-6-methylbenzothiazole,
2-(4-(1-hydroxy-4-methoxy-2-phenyldiazo)-phenyl)-6-methylbenzothiazole,
2-(4-(1-carboxy-4-hydroxy-3-phenyldiazo)-phenyl)-6-methylbenzothiazole,
2-(4-(4-hydroxy-1-methoxycarbonyl-3-phenyldiazo)-phenyl)-6-methylbenzothiazole,
2-(4-(1-hydroxy-2-methyl-4-phenyldiazo)-phenyl)-6-methylbenzothiazole,
2-(4-(1-hydroxy-2-methoxy-4-phenyldiazo)-phenyl)-6-methylbenzothiazole, 2-(4-(1-carboxy-2-hydroxy-5-phenyldiazo)-6-methyl-benzothiazole, and
2-(4-(2-hydroxy-1-methoxycarbonyl-5-phenyldiazo)-phenyl)-6-methylbenzothiazole.

EXAMPLE 35

2-(4-(phenyldiazo)-phenyl)-benzothiazoles Formula XX

Repeating the procedure of Example 33 but replacing 2-iodophenol with N-methyl-2-iodoaniline, N,N-dimethyl-2-iodoaniline, N-methylaniline and N,N-dimethylaniline yields the corresponding 2-(4-(2-iodo-1-methylamino-4-phenyldiazo)-phenyl)-6-methylbenzothiazole,
2-(4-(1-dimethylamino-2-iodo-4-phenyldiazo)-phenyl)-6-methylbenzothiazole,
2-(4-(1-methylamino-4-phenyldiazo)-phenyl)-6-methyl-benzothiazole, and
2-(4-(1,1-dimethylamino-4-phenyldiazo)-phenyl)-6-methylbenzothiazole-7-sulfonic acid.

EXAMPLE 36

2-(4-(iodophenyldiazo)-phenyl)-benzothiazoles Formulas XX and IV

Repeating the procedure of Example 2, but replacing BOR with the non-iodinated products of Examples 28–35 yields the following iodinated compounds, the iodo group being non-radioactive iodo, $^{123}I$ or $^{125}I$, depending upon whether the iodine source is non-radioactive ICl, $^{123}ICl$ or $^{125}ICl$:

2-(4-(1-hydroxy-2-iodo-4-phenyldiazo)-phenyl)-6-methylbenzothiazole-7-sulfonic acid,
2-(4-(1-hydroxy-2-iodo-4-methyl-6-phenyldiazo)-phenyl)-6-methylbenzo-thiazole-7-sulfonic acid,
2-(4-(1-hydroxy-2-iodo-4-methoxy-6-phenyldiazo)-phenyl)-6-methylbenzo-thiazole-7-sulfonic acid,
2-(4-(1-carboxy-3-iodo-4-hydroxy-5-phenyldiazo)-phenyl)-6-methylbenzo-thiazole-7-sulfonic acid,
2-(4-(4-hydroxy-3-iodo-1-methoxycarbonyl-5-phenyldiazo)-phenyl)-6-methylbenzothiazole-7-sulfonic acid,
2-(4-(1-hydroxy-2-iodo-6-methyl-4-phenyldiazo)-phenyl)-6-methylbenzo-thiazole-7-sulfonic acid,
2-(4-(1-hydroxy-2-iodo-6-methoxy-4-phenyldiazo)-phenyl)-6-methybenzo-thiazole-7-sulfonic acid,
2-(4-(1-carboxy-2-hydroxy-3-iodo-5-phenyldiazo)-phenyl)-6-methylbenzothiazole-7-sulfonic acid,
2-(4-(2-hydroxy-3-iodo-1-methoxycarbonyl-5-phenyldiazo)-phenyl)-6-methylbenzothiazole-7-sulfonic acid,
2-(4-(2-iodo-1-methylamino-4-phenyldiazo)-phenyl)-6-methylbenzothiazole-7-sulfonic acid,
2-(4-(2-iodo-1,1-dimethylamino-4-phenyldiazo)-phenyl)-6-methylbenzothiazole-7-sulfonic acid,
2-(4-(1-hydroxy-2-iodo-4-phenyldiazo)-phenyl)-6-methylbenzothiazole,
2-(4-(1-hydroxy-2-iodo-4-methyl-6-phenyldiazo)-phenyl)-6-methylbenzothiazole,
2-(4-(1-hydroxy-2-iodo-4-methoxy-6-phenyldiazo)-phenyl)-6-methylbenzothiazole,
2-(4-(1-carboxy-4-hydroxy-3-iodo-5-phenyldiazo)-phenyl)-6-methylbenzothiazole,
2-(4-(4-hydroxy-3-iodo-1-methoxycarbonyl-5-phenyldiazo)-phenyl)-6-methylbenzothiazole,
2-(4-(1-hydroxy-2-iodo-6-methyl-4-phenyldiazo)-phenyl)-6-methylbenzothiazole,
2-(4-(1-hydroxy-2-iodo-6-methoxy-4-phenyldiazo)-phenyl)-6-methybenzothiazole,
2-(4-(1-carboxy-2-hydroxy-3-iodo-5-phenyldiazo)-phenyl)-6-methylbenzothiazole,
2-(4-(2-hydroxy-3-iodo-1-methoxycarbonyl-5-phenyldiazo)-phenyl)-6-methylbenzothiazole,
2-(4-(2-iodo-1-methylamino-4-phenyldiazo)-phenyl)-6-methylbenzothiazole,
2-(4-(2-iodo-1,1-dimethylamino-4-phenyldiazo)-phenyl)-6-methylbenzothiazole-7-sulfonic acid,
2-(4-(1-hydroxy-2-iodo-4-phenyldiazo)-phenyl)-6-methylbenzothiazole-6-carboxylic acid,
2-(4-(1-hydroxy-2-iodo-4-methyl-6-phenyldiazo)-phenyl)-6-methylbenzothiazole-6-carboxylic acid,
2-(4-(1-hydroxy-2-iodo-4-methoxy-2-phenyldiazo)-phenyl)-6-methylbenzothiazole-6-carboxylic acid,
2-(4-(1-carboxy-4-hydroxy-3-iodo-5-phenyldiazo)-phenyl)-6-methybenzothiazole-6-carboxylic acid,
2-(4-(4-hydroxy-3-iodo-1-methoxycarbonyl-5-phenyldiazo)-phenyl)-6-methylbenzothiazole-6-carboxylic acid,
2-(4-(1-hydroxy-2-iodo-6-methyl-4-phenyldiazo)-phenyl)-6-methylbenzothiazole-6-carboxylic acid,
2-(4-(1-hydroxy-2-iodo-6-methoxy-4-phenyldiazo)-phenyl)-6-methylbenzothiazole-6-carboxylic acid,
2-(4-(1-carboxy-2-hydroxy-3-iodo-5-phenyldiazo)-phenyl)-6-methylbenzothiazole-6-carboxylic acid,
2-(4-(2-hydroxy-3-iodo-1-methoxycarbonyl-5-phenyldiazo)-phenyl)-6-methylbenzothiazole-6-carboxylic acid,
2-(4-(2-iodo-1-methylamino-4-phenyldiazo)-phenyl)-6-methylbenzothiazole-6-carboxylic acid, and
2-(4-(2-iodo-1,1-dimethylamino-4-phenyldiazo)-phenyl)-6-methylbenzothiazole-6-carboxylic acid.

EXAMPLE 37

2-(4-(iodophenyldiazo)-phenyl)-benzothiazoles Formula IV

Repeating the iodine exchange procedure of Example 3 but replacing the IBOR with the non-radioactive iodinated products of Examples 27–35 yields the following $^{125}I$ and $^{123}I$ products wherein iodo(*) represents either $^{125}I$ or $^{123}I$:

2-(4-(1-hydroxy-2-iodo(*)phen-4-yldiazo)-phenyl)-6-methylbenzothiazole-7-sulfonic acid,
2-(4-(1-hydroxy-4-iodo(*)phen-2-yldiazo)-phenyl)-6-methylbenzothiazole-7-sulfonic acid,
2-(4-(1-hydroxy-4-iodo(*)-2-methyl-6-phenyldiazo)-phenyl)-6-methylbenzothiazole-7-sulfonic acid,
2-(4-(1-hydroxy-4-iodo(*)-2-methoxy-6-phenyldiazo)-phenyl)-6-methylbenzothiazole-7-sulfonic acid,
2-(4-(1-carboxy-2-hydroxy-5-iodo(*)-3-phenyldiazo)-phenyl)-6-methylbenzothiazole-7-sulfonic acid,
2-(4-(2-hydroxy-5-iodo(*)-1-methoxycarbonyl-3-phenyldiazo)-phenyl)-6-methylbenzothiazole-7-sulfonic acid,
2-(4-(1-hydroxy-2-iodo(*)-6-methyl-4-phenyldiazo)-phenyl)-6-methylbenzothiazole-7-sulfonic acid,
2-(4-(1-hydroxy-2-iodo(*)-6-methoxy-4-phenyldiazo)-phenyl)-6-methylbenzothiazole-7-sulfonic acid,
2-(4-(1-carboxy-2-hydroxy-3-iodo(*)-5-phenyldiazo)-phenyl)-6-methylbenzothiazole-7-sulfonic acid,
2-(4-(2-hydroxy-3-iodo(*)-1-methoxycarbonyl-5-phenyldiazo)-phenyl)-6-methylbenzothiazole-7-sulfonic acid, 2-(4-(1-hydroxy-2-iodo(*)-4-methyl-6-phenyldiazo)-phenyl)-6-methylbenzothiazole-7-sulfonic acid,
2-(4-(1-hydroxy-2-iodo(*)-4-methoxy-6-phenyldiazo)-phenyl)-6-methylbenzothiazole-7-sulfonic acid,
2-(4-(1-carboxy-4-hydroxy-3-iodo(*)-5-phenyldiazo)-phenyl)-6-methylbenzothiazole-7-sulfonic acid,
2-(4-(4-hydroxy-3-iodo(*)-1-methoxycarbonyl-5-phenyldiazo)-phenyl)-6-methylbenzothiazole-7-sulfonic acid,
2-(4-(1-methylamino-2-iodo(*)-4-phenyldiazo)-phenyl)-6-methylbenzothiazole-7-sulfonic acid,
2-(4-(1,1-dimethylamino-2-iodo(*)-4-phenyldiazo)-phenyl)-6-methylbenzothiazole-7-sulfonic acid,
2-(4-(1-hydroxy-4-iodo(*)phen-2-yldiazo)-phenyl)-6-methylbenzothiazole,
2-(4-(1-hydroxy-4-iodo(*)-2-methyl-6-phenyldiazo)-phenyl)-6-methylbenzothiazole,
2-(4-(1-hydroxy-4-iodo(*)-2-methoxy-6-phenyldiazo)-phenyl)-6-methylbenzothiazole,
2-(4-(1-carboxy-2-hydroxy-5-iodo(*)-3-phenyldiazo)-phenyl)-6-methylbenzothiazole,
2-(4-(2-hydroxy-5-iodo(*)-1-methoxycarbonyl-3-phenyldiazo)-phenyl)-6-methylbenzothiazole,
2-(4-(1-hydroxy-2-iodo(*)-6-methyl-4-phenyldiazo)-phenyl)-6-methylbenzothiazole,
2-(4-(1-hydroxy-2-iodo(*)-6-methoxy-4-phenyldiazo)-phenyl)-6-methylbenzothiazole,
2-(4-(1-carboxy-2-hydroxy-3-iodo(*)-5-phenyldiazo)-phenyl)-6-methylbenzothiazole,
2-(4-(2-hydroxy-3-iodo(*)-1-methoxycarbonyl-5-phenyldiazo)-phenyl)-6-methylbenzothiazole,
2-(4-(1-hydroxy-2-iodo(*)-4-methoxy-6-phenyldiazo)-phenyl)-6-methylbenzothiazole,
2-(4-(1-carboxy-4-hydroxy-3-iodo(*)-5-phenyldiazo)-phenyl)-6-methylbenzothiazole,
2-(4-(4-hydroxy-3-iodo(*)-1-methoxycarbonyl-5-phenyldiazo)-phenyl)-6-methylbenzothiazole,
2-(4-(1-methylamino-2-iodo(*)-4-phenyldiazo)-phenyl)-6-methylbenzothiazole,
2-(4-(1,1-dimethylamino-2-iodo(*)-4-phenyldiazo)-phenyl)-6-methylbenzothiazole,
2-(4-(1-hydroxy-4-iodo(*)phen-2-yldiazo)-phenyl)-6-methylbenzothiazole-6-carboxylic acid,
2-(4-(1-hydroxy-4-iodo(*)-2-methyl-6-phenyldiazo)-phenyl)-6-methylbenzothiazole-6-carboxylic acid,
2-(4-(1-hydroxy-4-iodo(*)-2-methoxy-6-phenyldiazo)-phenyl)-6-methylbenzothiazole-6-carboxylic acid,
2-(4-(1-carboxy-2-hydroxy-5-iodo(*)-3-phenyldiazo)-phenyl)-6-methylbenzothiazole-6-carboxylic acid,
2-(4-(2-hydroxy-5-iodo(*)-1-methoxycarbonyl-3-phenyldiazo)-phenyl)-6-methylbenzothiazole-6-carboxylic acid,
2-(4-(1-hydroxy-2-iodo(*)-6-methyl-4-phenyldiazo)-phenyl)-6-methylbenzothiazole-6-carboxylic acid,
2-(4-(1-hydroxy-2-iodo(*)-6-methoxy-4-phenyldiazo)-phenyl)-6-methylbenzothiazole-6-carboxylic acid,
2-(4-(1-carboxy-2-hydroxy-3-iodo(*)-5-phenyldiazo)-phenyl)-6-methylbenzothiazole-6-carboxylic acid,
2-(4-(2-hydroxy-3-iodo(*)-1-methoxycarbonyl-5-phenyldiazo)-phenyl)-6-methylbenzothiazole-6-carboxylic acid,
2-(4-(1-hydroxy-2-iodo(*)-4-methyl-6-phenyldiazo)-phenyl)-6-methylbenzothiazole-6-carboxylic acid,
2-(4-(1-hydroxy-2-iodo(*)-4-methoxy-6-phenyldiazo)-phenyl)-6-methylbenzothiazole-6-carboxylic acid,
2-(4-(1-carboxy-4-hydroxy-3-iodo(*)-5-phenyldiazo)-phenyl)-6-methylbenzothiazole-6-carboxylic acid,
2-(4-(4-hydroxy-3-iodo(*)-1-methoxycarbonyl-5-phenyldiazo)-phenyl)-6-methylbenzothiazole-6-carboxylic acid,
2-(4-(1-methylamino-2-iodo(*)-4-phenyldiazo)-phenyl)-6-methylbenzothiazole-6-carboxylic acid,
2-(4-(1,1-dimethylamino-2-iodo(*)-4-phenyldiazo)-phenyl)-6-methylbenzothiazole-6-carboxylic acid,
2-(4-(1-hydroxy-2-iodo(*)-4-phenyldiazo)-phenyl)-6-methylbenzothiazole-7-sulfonic acid,
2-(4-(1-hydroxy-2-iodo(*)-4-methyl-6-phenyldiazo)-phenyl)-6-methylbenzothiazole-7-sulfonic acid,
2-(4-(1-hydroxy-2-iodo(*)-4-methoxy-6-phenyldiazo)-phenyl)-6-methylbenzothiazole-7-sulfonic acid,
2-(4-(1-carboxy-3-iodo(*)-4-hydroxy-5-phenyldiazo)-phenyl)-6-methylbenzothiazole-7-sulfonic acid,
2-(4-(4-hydroxy-3-iodo(*)-1-methoxycarbonyl-5-phenyldiazo)-phenyl)-6-methylbenzothiazole-7-sulfonic acid,
2-(4-(1-hydroxy-2-iodo(*)-6-methyl-4-phenyldiazo)-phenyl)-6-methylbenzothiazole-7-sulfonic acid,
2-(4-(1-hydroxy-2-iodo(*)-6-methoxy-4-phenyldiazo)-phenyl)-6-methylbenzothiazole-7-sulfonic acid,
2-(4-(1-carboxy-2-hydroxy-3-iodo(*)-5-phenyldiazo)-phenyl)-6-methylbenzothiazole-7-sulfonic acid,
2-(4-(2-hydroxy-3-iodo(*)-1-methoxycarbonyl-5-phenyldiazo)-phenyl)-6-methylbenzothiazole-7-sulfonic acid,
2-(4-(2-iodo(*)-1-methylamino-4-phenyldiazo)-phenyl)-6-methylbenzothiazole-7-sulfonic acid,
2-(4-(2-iodo(*)-1,1-dimethylamino-4-phenyldiazo)-phenyl)-6-methylbenzothiazole-7-sulfonic acid,
2-(4-(1-hydroxy-2-iodo(*)-4-phenyldiazo)-phenyl)-6-methylbenzothiazole,
2-(4-(1-hydroxy-2-iodo(*)-4-methyl-6-phenyldiazo)-phenyl)-6-methylbenzothiazole,
2-(4-(1-hydroxy-2-iodo(*)-4-methoxy-6-phenyldiazo)-phenyl)-6-methylbenzothiazole,
2-(4-(1-carboxy-4-hydroxy-3-iodo(*)-5-phenyldiazo)-phenyl)-6-methylbenzothiazole,
2-(4-(4-hydroxy-3-iodo(*)-1-methoxycarbonyl-5-phenyldiazo)-phenyl)-6-methylbenzothiazole,
2-(4-(1-hydroxy-2-iodo(*)-6-methyl-4-phenyldiazo)-phenyl)-6-methylbenzothiazole,
2-(4-(1-hydroxy-2-iodo(*)-6-methoxy-4-phenyldiazo)-phenyl)-6-methylbenzothiazole,
2-(4-(1-carboxy-2-hydroxy-3-iodo(*)-5-phenyldiazo)-phenyl)-6-methylbenzothiazole,
2-(4-(2-hydroxy-3-iodo(*)-1-methoxycarbonyl-5-phenyldiazo)-phenyl)-6-methylbenzothiazole,
2-(4-(2-iodo(*)-1-methylamino-4-phenyldiazo)-phenyl)-6-methylbenzothiazole,
2-(4-(2-iodo(*)-1,1-dimethylamino-4-phenyldiazo)-phenyl)-6-methylbenzothiazole-7-sulfonic acid,
2-(4-(1-hydroxy-2-iodo(*)-4-phenyldiazo)-phenyl)-6-methylbenzothiazole-6-carboxylic acid,
2-(4-(1-hydroxy-2-iodo(*)-4-methyl-6-phenyldiazo)-phenyl)-6-methylbenzothiazole-6-carboxylic acid,
2-(4-(1-hydroxy-2-iodo(*)-4-methoxy-2-phenyldiazo)-phenyl)-6-methylbenzothiazole-6-carboxylic acid,
2-(4-(1-carboxy-4-hydroxy-3-iodo(*)-5-phenyldiazo)-phenyl)-6-methylbenzothiazole-6-carboxylic acid,
2-(4-(4-hydroxy-3-iodo(*)-1-methoxycarbonyl-5-phenyldiazo)-phenyl)-6-methylbenzothiazole-6-carboxylic acid,
2-(4-(1-hydroxy-2-iodo(*)-6-methyl-4-phenyldiazo)-phenyl)-6-methylbenzothiazole-6-carboxylic acid,
2-(4-(1-hydroxy-2-iodo(*)-6-methoxy-4-phenyldiazo)-phenyl)-6-methylbenzothiazole-6-carboxylic acid, 2-(4-(1-carboxy-2-hydroxy-3-iodo(*)-5-phenyldiazo)-phenyl)-6-methylbenzothiazole-6-carboxylic acid, 2-(4-(2-hydroxy-3-iodo(*)-1-methoxycarbonyl-5-phenyldiazo)-phenyl)-6-methylbenzothiazole-6-carboxylic acid, 2-(4-(2-iodo(*)-1-methylamino-4-phenyldiazo)-phenyl)-6-methylbenzothiazole-6-carboxylic acid, and 2-(4-(2-iodo(*)-1,1-dimethylamino-4-phenyldiazo)-phenyl)-6-methylbenzothiazole-6-carboxylic acid.

We claim:

1. An amyloid binding diazo compound of the following formula, or a water-soluble non-toxic salt thereof:

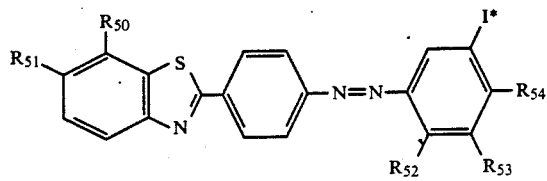

wherein:
I* is a radioactive iodine moiety;
$R_{50}$ is hydrogen or sulfo;
$R_{51}$ is methyl or carboxyl; and
$R_{52}$, $R_{53}$ and $R_{54}$ each are hydrogen, hydroxy, carboxy or lower alkyl esters thereof, methyl or methoxy.

2. As a compound of claim 1, 2-(4-(1-hydroxy-2-$^{123}$I-phen-4-yldiazo)-phenyl)-6-methylbenzothiazole-7-sulfonic acid or a water-soluble, non-toxic salt thereof.

3. As a compound of claim 1, 2-(4-(1-hydroxy-2-$^{124}$I-phen-4-yldiazo)-phenyl)-6-methylbenzothiazole-7-sulfonic acid or a water-soluble, non-toxic salt thereof.

4. A method for determining the presence and location of an amyloid deposit in a body area of a patient, comprising intravenous administration of an imaging effective quantity of a compound containing a radioactive iodine group of any one of claims 1, 2 or 3 to the patient, and sensing radiation emitted from the body area.

* * * * *